(12) United States Patent
Chaux et al.

(10) Patent No.: US 6,710,172 B1
(45) Date of Patent: Mar. 23, 2004

(54) TUMOR ANTIGENS AND CTL CLONES ISOLATED BY A NOVEL PROCEDURE

(75) Inventors: Pascal Chaux, Issurtille (FR); Rosalie Luiten, Brussels (BE); Nathalie Demotte, Brussels (BE); Marie-Therese Duffour, Paris (FR); Christophe Lurquin, Brussels (BE); Catie Traversari, Milan (IT); Vincent Stroobant, Brussels (BE); Guy R. Cornelis, Brussels (BE); Thierry Boon-Falleur, Brussels (BE); Pierre van der Bruggen, Brussels (BE); Erwin Schultz, Erlangen (DE); Guy Warnier, Brussels (BE)

(73) Assignee: Ludwig Institute For Cancer Research, New York, NY (US)

( * ) Notice: Subject to any disclaimer, the term of this patent is extended or adjusted under 35 U.S.C. 154(b) by 0 days.

(21) Appl. No.: 09/806,769

(22) PCT Filed: Sep. 15, 1999

(86) PCT No.: PCT/IB99/01664

§ 371 (c)(1),
(2), (4) Date: Jul. 30, 2001

(87) PCT Pub. No.: WO00/20445

PCT Pub. Date: Apr. 13, 2000

Related U.S. Application Data

(63) Continuation-in-part of application No. 09/289,350, filed on Apr. 9, 1999, now Pat. No. 6,531,451, which is a continuation-in-part of application No. 09/165,863, filed on Oct. 2, 1998, now Pat. No. 6,407,063.

(51) Int. Cl.[7] ............................................. C07H 21/04
(52) U.S. Cl. ..................................................... 536/23.5
(58) Field of Search ....................................... 536/23.5

*Primary Examiner*—Christina Chan
*Assistant Examiner*—Marianne DiBrino
(74) *Attorney, Agent, or Firm*—Scully, Scott, Murphy & Presser

(57) ABSTRACT

The present invention relates to nucleic acid molecules encoding antigenic peptides from MAGE molecules that bind to HLA. An example of the nucleic acid molecules of the present invention is a nucleic acid molecule coding for the peptide GVYDGREHTV (SEQ ID NO: 44), which peptide binds to HLA-A2. The nucleic acid molecules and the encoded antigenic peptides are useful for diagnosing and treating various pathological conditions.

1 Claim, 13 Drawing Sheets

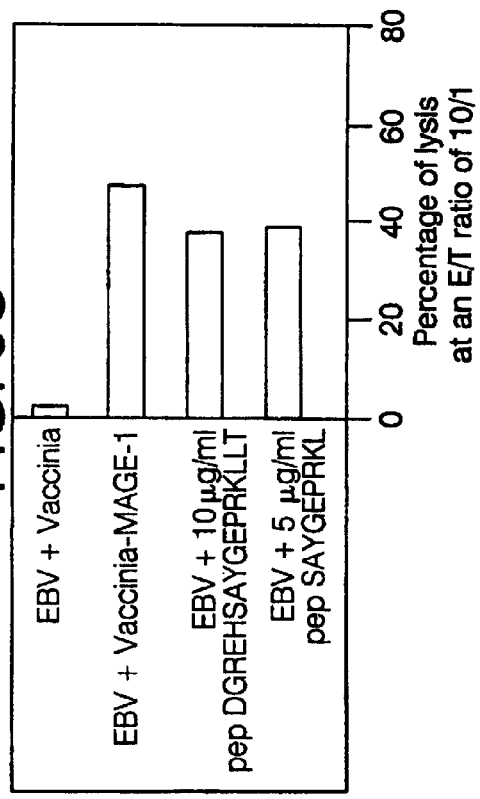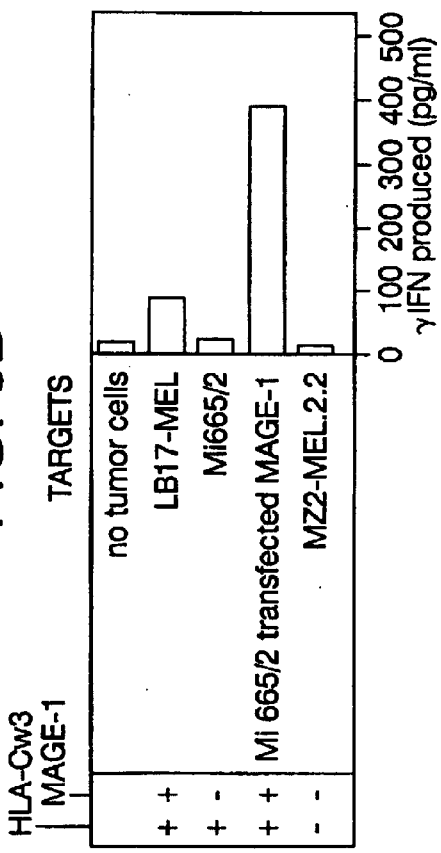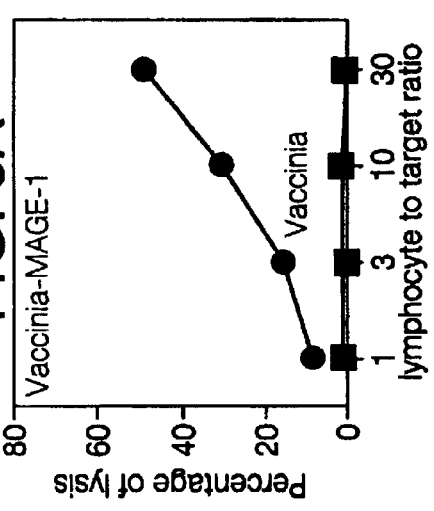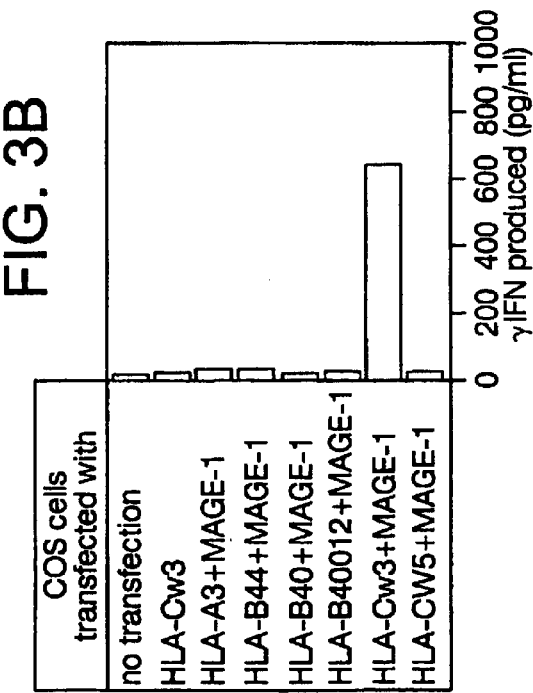

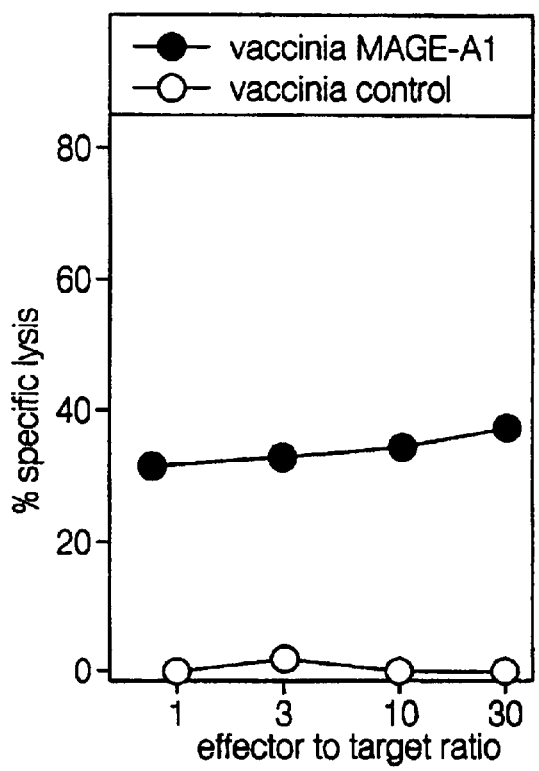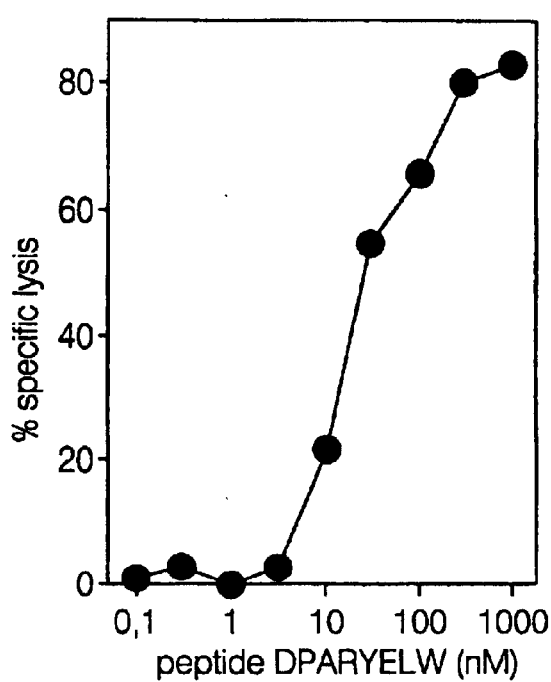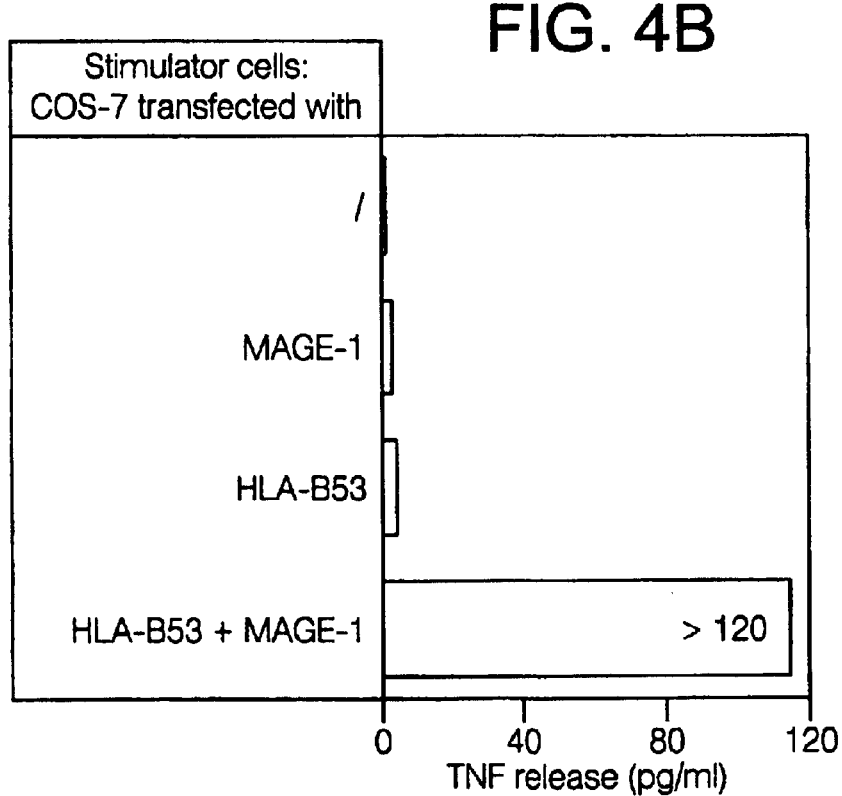

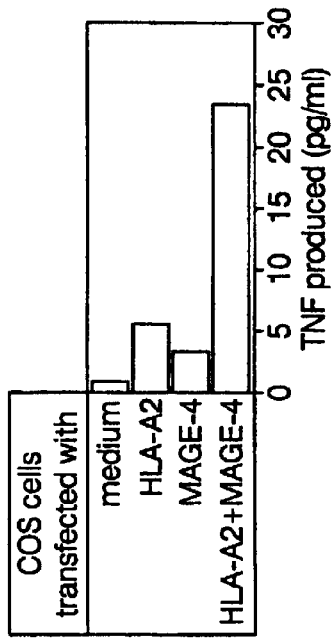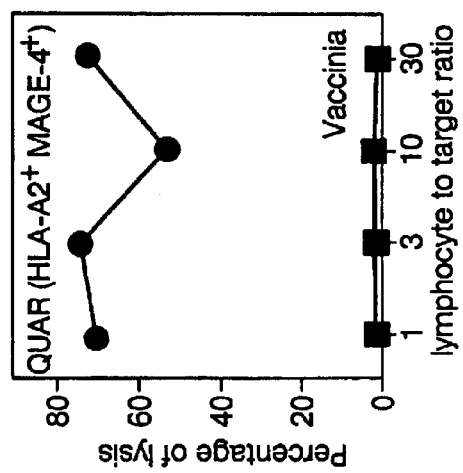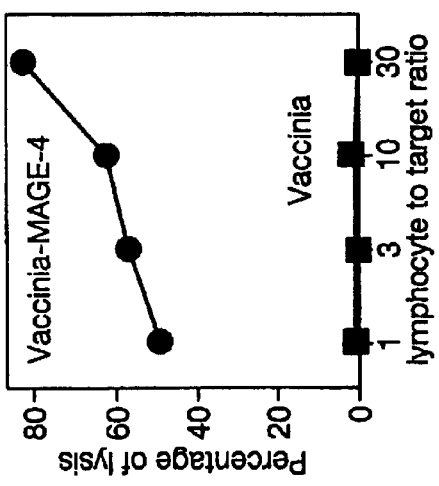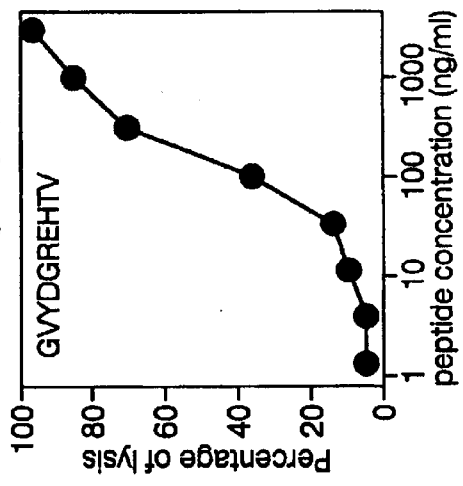

FIG. 6

AGTCATCATGTCTTCTGAGCAGAAGAGTCAGCACTGCAAGCCTGAGGA
→ S

AGGCGTTGAGGCCCAAGAAGAGGCCCTGGGCCTGGTGGGTGCACAGGC
← AS8

TCCTACTACTGAGGAGCAGGAGGCTGCTGTCTCCTCCTCCTCTCCTCTG

GTCCCTGGCACCCTGGAGGAAGTGCCTGCTGCTGAGTCAGCAGGTCCTC
← AS7

CCCAGAGTCCTCAGGGAGCCTCTGCCTTACCCACTACCATCAGCTTCA

CTTGCTGGAGGCAACCCAATGAGGGTTCCAGCAGCCAAGAAGAGGAGG

GGCCAAGCACCTCGCCTGACGCAGAGTCCTTGTTCCGAGAAGCACTCA
← AS6

GTAACAAGGTGGATGAGTTGGCTCATTTTCTGCTCCGCAAGTATCGAG

CCAAGGAGCTGGTCACAAAGGCAGAAATGCTGGAGAGAGTCATCAAA
←

AATTACAAGCGCTGCTTTCCTGTGATCTTCGGCAAAGCCTCCGAGTCC
AS5

CTGAAGATGATCTTTGGCATTGACGTGAAGGAAGTGGACCCCGCCAGC

AACACCTACACCCTTGTCACCTGCCTGGGCCTTTCCTATGATGGCCTG
← AS4

CTGGGTAATAATCAGATCTTTCCCAAGACAGGCCTTCTGATAATCGTC

CTGGGCACAATTGCAATGGAGGGCGACAGCGCCTCTGAGGAGGAAATC

TGGGAGGAGCTGGGTGTGATGGGGGTGTATGATGGGAGGGAGCACACT
← AS3

GTCTATGGGGAGCCCAGGAAACTGCTCACCCAAGATTGGGTGCAGGAA

AACTACCTGGAGTACCGGCAGGTACCCGGCAGTAATCCTGCGCGCTAT
←

GAGTTCCTGTGGGGTCCAAGGGCTCTGGCTGAAACCAGCTATGTGAAA
AS2

GTCCTGGAGCATGTGGTCAGGGTCAATGCAAGAGTTCGCATTGCCTAC

CCATCCCTGCGTGAAGCAGCTTTGTTAGAGGAGGAAGAGGGAGTCTGA
← AS1

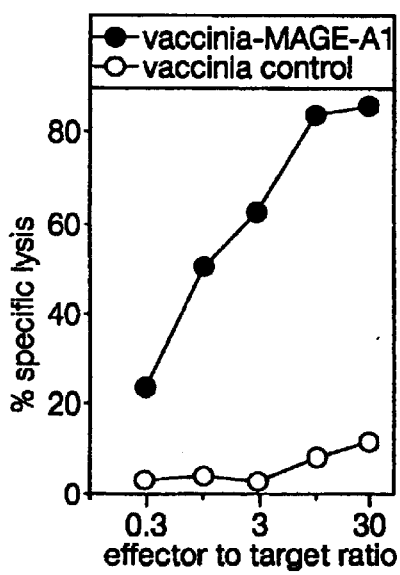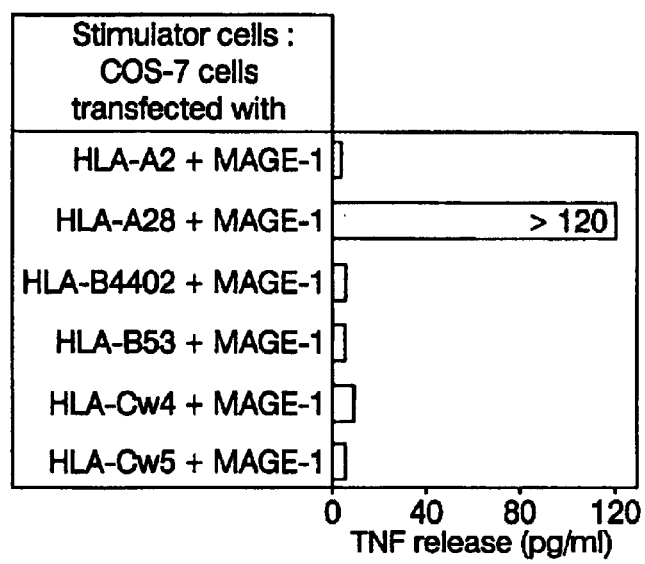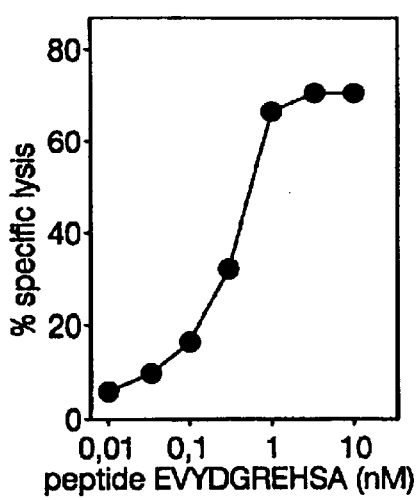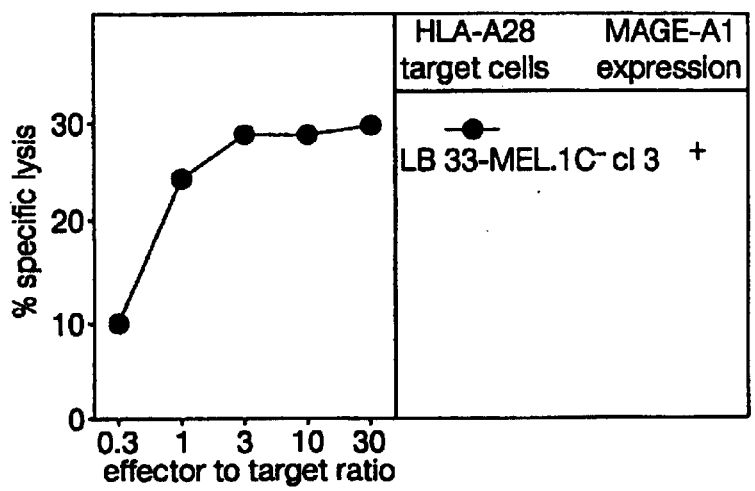

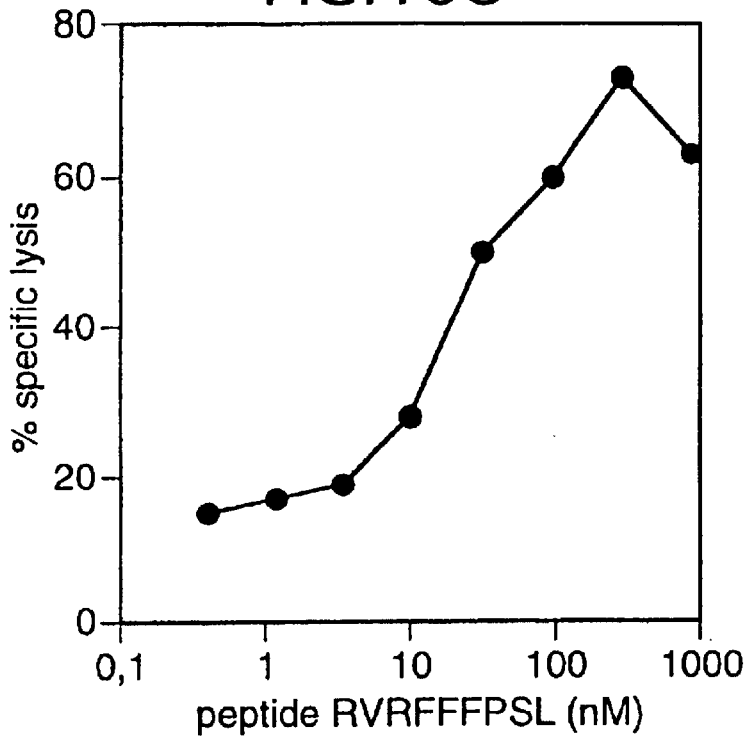
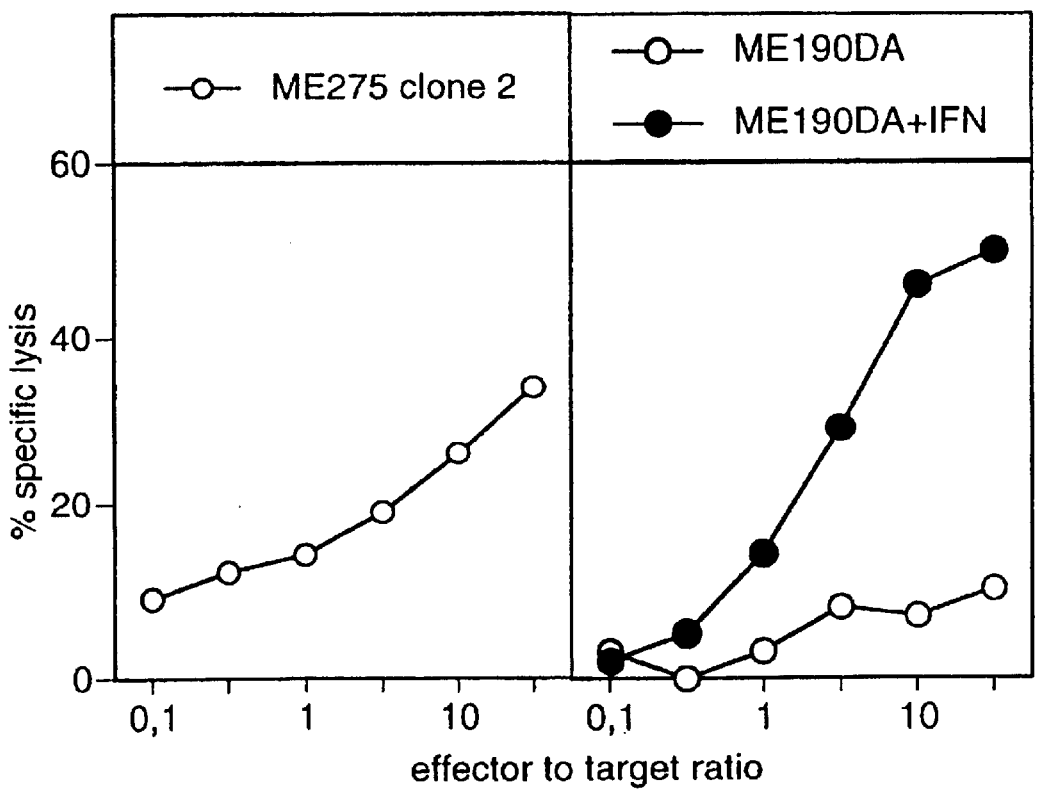

TUMOR ANTIGENS AND CTL CLONES ISOLATED BY A NOVEL PROCEDURE

CROSS REFERENCE TO RELATED APPLICATIONS

This application is a 371 of PCT/IB99/01664, filed on Sep. 15, 1999, which is a continuation-in-part of U.S. Ser. No. 09/289,350, filed on Apr. 9, 1999, now U.S. Pat. No. 6,531,451, which is a continuation-in-part of U.S. Ser. No. 09/165,863, filed on Oct. 2, 1998, now U.S. Pat. No. 6,407,063.

FIELD OF INVENTION

The present invention relates to isolation of cytotoxic T lymphocyte (CTL) clones. The CTL clones of the present invention have been isolated by successive steps of stimulation and testing of lymphocytes with antigen presenting cells which present antigens derived from different expression systems, e.g., from recombinant Yersinia, recombinant Salmonella, or recombinant viruses. The present invention further relates to isolated CTL clones that are specific for proteins of the MAGE family. Antigenic peptides as well as the peptide/HLA complexes which are recognized by the isolated CTL clones are also provided.

BACKGROUND

An important facet of the immune response in a mammalian subject is the recognition by T cells of the complexes of the cell surface molecules, i.e., the complexes of peptides and HLA (human leukocyte antigens) or MHC (major histocompatibility complexes) molecules. These peptides are derived from larger molecules which are processed by the cells which also present the HLA/MHC molecules. See in this regard, Male et al., *Advanced Immunology* (J. P. Lipincott Company, 1987), especially chapters 6–10. The interaction between T cell and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system response to foreign materials, in autoimmune pathologies, and in responses to cellular abnormalities.

Most progressively growing neoplastic cells express potentially immunogenic tumor-associated antigens (TAAs), also called tumor rejection antigens (TRAs). A number of genes have been identified that encode tumor rejection antigen precursors (or TRAPs), which are processed into TRAs in tumor cells. Such TRAP-encoding genes include members of the MAGE family, the BAGE family, the DAGE/PRAME family, the GAGE family, the RAGE family, the SMAGE family, NAG, Tyrosinase, Melan-A/MART-1, gp 100, MUC-1, TAG-72, CA125, mutated proto-oncogenes such as praise, mutated tumor suppressor genes such as p53, tumor associated viral antigens such as HPV16 E7. See, e.g., review by Van den Eynde and van der Bruggen (1997) in *Curr. Opin. Immunol.* 9:684–693, Sahin et al. (1997) in *Curr. Opin. Immunol.* 9:709–716, and Shawler et al. (1997) *Advances in Pharmacology* 40: 309–337, Academic Press, Inc., San Diego, Calif.

TRAs, like other antigenic epitopes, are presented at the surface of tumor cells by MHC molecules and have been shown to induce a CTL response in vivo and in vitro. See, for example, van der Bruggen et al. (1991) *Science* 254: 1643–1647. However, such TRA expressing tumor cells do not provoke reliable anti-tumor immune responses in vivo that are capable of controlling the growth of malignant cells. Boon et al. (1992) *Cancer Surveys* 13: 23–37; T. Boon (1993) *Int. J. Cancer* 54: 177–180; T. Boon (1992) *Advances Cancer Res.* 58: 177–209. Thus, generation of CTL clones that recognize specific TRAs provides a powerful tool for tumor therapeutics. The identification of TRAs also allows the design of recombinant vaccines for the treatment of various pathological conditions.

The present invention provides a novel procedure for isolating CTL clones. By following such procedure, novel CTL clones have been isolated that recognize specific antigenic peptides of proteins, preferably of the MAGE family. The MHC molecules presenting these peptides have been identified as well.

SUMMARY OF THE INVENTION

One embodiment of the present invention provides methods for isolating CTL clones from a blood sample.

The methods of the present invention include successive steps of stimulating and testing lymphocytes with antigen presenting cells. Such methods, by employing different antigen presenting cells at different steps, significantly reduce non-specific CTL activities generated in the procedure and permit more efficient isolation of CTL clones.

Antigen presenting cells which are used in the methods of the present invention can differ in cell type and/or in the expression system from which the antigen to be presented is derived. Cells which can be employed as antigen presenting cells in the present methods include professional and facultative antigen presenting cells. A preferred antigen presenting cell is an autologous dendritic cell, an autologous B cell transformed with EBV, or an activated T cell.

Antigen presenting cells can be modified by a variety of ways to effect the expression of an antigen of interest at the cell surface, preferably, by infection with a recombinant Yersinia, recombinant Salmonella, or recombinant viruses. Preferred recombinant viruses include vaccinia, canarypox virus, other pox viruses, adenovirus, herpes simplex virus, and retrovirus.

The protein against which CTL clones are generated can be a tumor associated protein, an antigenic protein of a pathogen, or the like. Preferably, the protein is a member of the MAGE family, in particular, MAGE-A1, MAGE-A3 and MAGE-A4.

In another embodiment, the present invention contemplates CTL clones isolated by using the methods of the present invention.

In a preferred embodiment, the present invention provides isolated CTL clones that are specific for peptide/HLA complexes SAYGEPRKL(SEQ ID NO: 2)/HLA-Cw3, DPARYEFLW(SEQ ID NO: 42)/HLA-B53, GVYDGREHTV(SEQ ID NO: 44)/HLA-A2, SAFPTTINF (SEQ ID NO: 47)/HLA-Cw2, EVYDGREHSA(SEQ ID NO: 48)/HLA-A28, AELVHFLLL (SEQ ID NO: 55)/HLA-B40, and RVRFFFPSL (SEQ ID NO: 57)/HLA-B7, respectively.

In a more preferred embodiment, the present invention provides isolated CTL clones LB1137 462/F3.2, LB1801 456/H7.11, LB1118 466/D3.31, LB 1801 456/H8.33, LB1137 H4.13, LB1841 526/F7.1 and LB1803 483/G8.4.

Furthermore, the present invention provides methods of identifying antigenic peptide epitopes of a protein by using CTL clones isolated following the methods of present invention.

In still another embodiment, the present invention provides newly isolated antigenic peptides, DPARYEFLW (MAGE-A1 258–266) (SEQ ID NO: 42), GVYDGREHTV (MAGE-A4 230–239) (SEQ ID NO: 44), SAFPTTINF(SEQ ID NO: 47) (MAGE-A1 62–70), EVYDGREHSA(SEQ ID NO: 48) (MAGE-A1 222–231), AELVHFLLL (SEQ ID NO: 55) (MAGE-A3 114–122), RVRFFFPSL (SEQ ID NO: 57) (MAGE-A1 289–297). Nucleic acid sequences encoding such peptides are also contemplated.

In another embodiment, the present invention provides isolated peptide/HLA complexes, peptide SAYGEPRKL (SEQ ID NO: 2) complexed with HLA-Cw3, peptide DPARYEFLW(SEQ ID NO: 42) complexed with HLA-B53, peptide GVYDGREHTV(SEQ ID NO: 44) complexed with HLA-A2, peptide SAFPTTINF(SEQ ID NO: 47) complexed with HLA-Cw2, EVYDGREHSA(SEQ ID NO: 48) complexed with HLA-A28, AELVHFLLL (SEQ ID NO: 55) complexed with HLA-B40, and RVRFFFPSL (SEQ ID NO: 57) complexed with HLA-B7.

In another embodiment, cells expressing any of these peptide/HLA complexes are contemplated.

Still another embodiment of the invention provides pharmaceutical compositions which include any one of the isolated CTL clones, the antigenic peptides, the peptide/HLA complexes, and cells expressing the peptide/HLA complexes of the present invention.

In a further aspect, the present invention provides methods useful for diagnosing and treating various pathological conditions.

One embodiment of the present invention provides methods of diagnosing in a subject, a pathological condition characterized by an abnormal expression of a peptide/HLA complex, by detecting the presence of cells abnormally expressing such complex in the subject.

Another embodiment of the present invention provides methods of detecting in a subject, the presence of cells abnormally expressing a peptide/HLA complex of the present invention by using an isolated CTL clone of the present invention which specifically recognizes such complex.

One embodiment of the present invention provides methods of diagnosing in a subject, a pathological condition characterized by an abnormal expression of a peptide/HLA complex, by detecting an increased frequency of CTL cells specific for such complex.

Another embodiment of the present invention provides methods of detecting in a subject the presence, of CTL cells specific for a peptide/HLA complex of the present invention by using an antigen presenting cell expressing such complex at the cell surface.

In still another embodiment, the present invention provides methods of treating a subject of a pathological condition characterized by an abnormal expression of a peptide/HLA complex of the present invention by administering to the subject, a therapeutically effective amount of cells of a CTL clone specific for such complex.

Another embodiment provides methods of treating a subject of a pathological condition characterized by an abnormal expression of a peptide/HLA complex of the present invention, by administering to the subject a therapeutically effective amount of the peptide.

Still another embodiment provides methods of treating a pathological condition characterized by an abnormal expression of a peptide/HLA complex of the present invention, by obtaining antigen presenting cells from the subject, modifying such cells to effect a presentation of the peptide/HLA complex at the cell surface, and then reperfusing such "loaded" cells into the subject.

BRIEF DESCRIPTION OF FIGURES

FIG. 2B depicts the quantitation of IFN-released by activated CTLs.

FIGS. 3A–D depict the specific recognition by CTL clone LB1137 462/H7.11 of a MAGE-A1 antigenic peptide (SEQ ID NO: 2) presented by HLA-B53.

FIGS. 4A–C depict the specific recognition by CTL clone LB1801 456/H7.11 of a MAGE-A1 antigenic peptide (SEQ ID NO: 42) presented by HLA-B53.

FIGS. 5A–D depict the specific recognition by CTL clone LB1137 H4.13 of a MAGE-A4 antigenic peptide (SEQ ID NO: 44) presented by HLA-A2.

FIG. 6 depicts the MAGE-A4 nucleotide sequences (SEQ ID NO: 49) and the primers used in PCR as described in Example 9.

Figure 1:
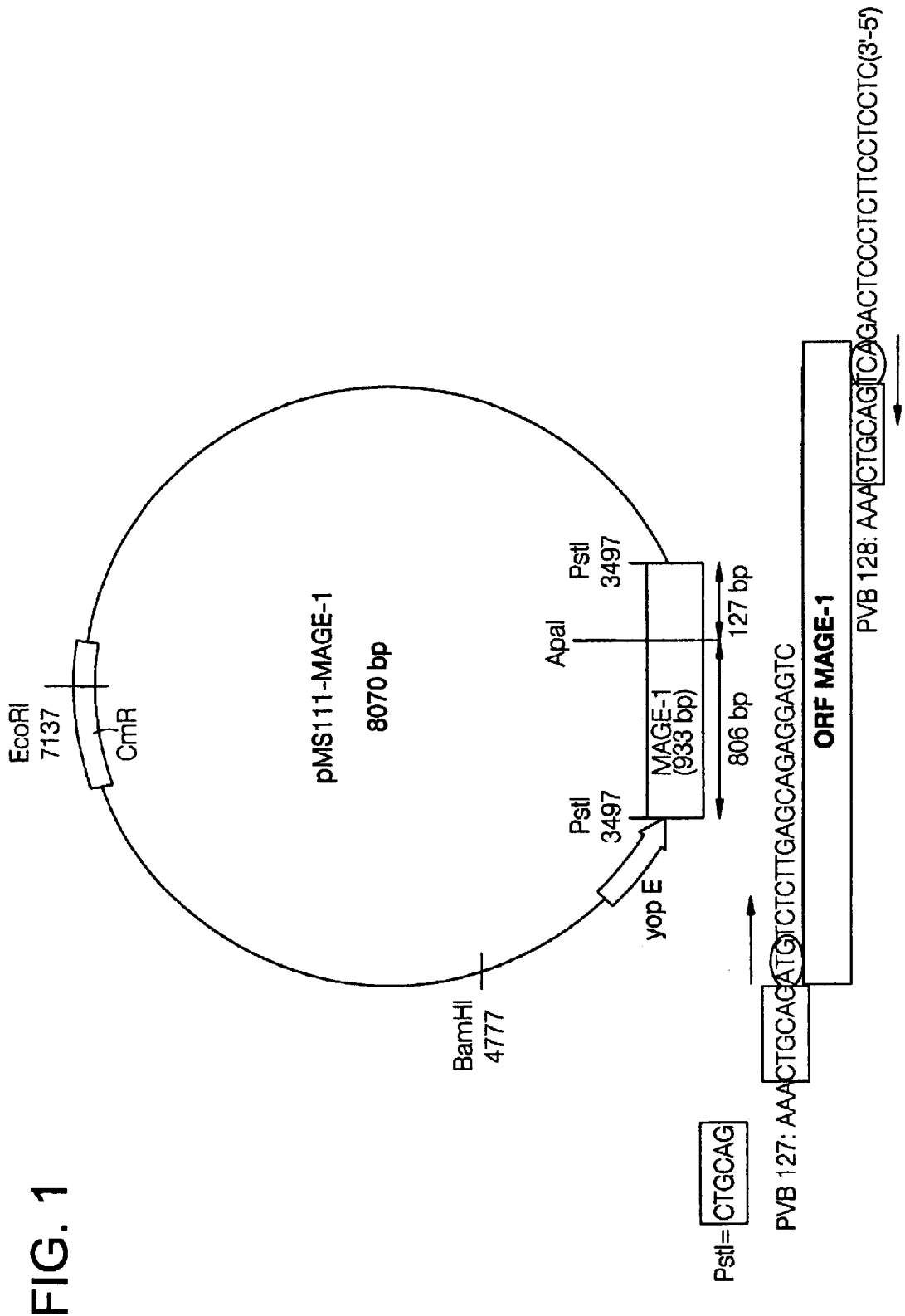
FIG. 1 illustrates the plasmid map of the expression vector pMS111-MAGE-A1 (YopE$_{130}$-MAGE-A1). The sequences of the primers PVB127 and PVB128 are set forth in SEQ ID NO: 33 and SEQ ID NO: 34, respectively.

7A. Lysis by CTL clone LB1118 466/D3.31 of autologous EBV-B cells infected with vaccinia-MAGE-A1. Target cells were infected for 2 hours at an MOI of 20, $^{51}$Cr-labeled, and incubated with CTL clone LB1118 466/D3.31 for 4 hours. Targets infected with the parental vaccinia were used as a negative control.

7B. Stimulation of CTL clone LB1118 466/D3.31 by COS-7 cells that were transiently transfected with a MAGE-A1 cDNA and a cDNA encoding HLA-Cw2. One day after transfection, 1,500 CTL clone LB1118 466/D3.31 were added into microwells containing 1.5×10$^4$ transfected COS-7 cells. TNF production was estimated after overnight coculture by testing the toxicity of the supernatants for the TNF-sensitive cells of WEHI-164 clone 13.

7C. Lysis by CTL clone LB1118 466/D3.31 of autologous EBV-B cells incubated with synthetic peptide SAFPTTINF (SEQ ID NO: 47) (MAGE-A1$_{62-70}$). Targets were $^{52}$Cr-labeled and incubated for 4 hours with the CTL, at an effector-to-target ratio of 5:1, in the presence of the peptide at the concentrations indicated.

7D. Lysis of HLA-Cw2 tumor cell lines by CTL clone LB1118 466/D3.31. Target cells were $^{51}$Cr-labeled and incubated for 4 hours with CTL clone LB1118 466/D3.31 at various effector-to-target ratios.

FIGS. 8A–D depict a MAGE-A1 peptide presented by HLA-A28 to CTL clone LB1801 456/H8.33.

8A. Lysis by CTL clone LB1801 456/H8.33 of autologous EBV-B cells infected with vaccinia-MAGE-A1. Target cells were infected for 2 hours at an MOI of 20, $^{51}$Cr labeled, and incubated with CTL clone LB1801 456/H8.33 for 4 hours. Targets infected with the parental vaccinia were used as a negative control.

8B. Stimulation of CTL clone LB1801 456/H8.33 by COS-7 cells transiently transfected with a MAGE-A1 cDNA and a cDNA encoding HLA-A28. One day after transfection, 1,500 CTL clone LB1801 456/H8.33 were added into microwells containing 1.5×10$^4$ transfected COS-7 cells.

TNF production was estimated after overnight coculture by testing the toxicity of the supernatants for the TNF-sensitive cells of WEHI-164 clone 13.

8C. Lysis by CTL clone LB1801 456/H8.33 of autologous EBV-B cells incubated with synthetic peptide EVYDGREHSA(SEQ ID NO: 48) (MAGE-A1$_{222\text{-}231}$). Targets were $^{51}$Cr-labeled and incubated for 4 hours with CTL clone LB1801 456/H8.33, at an effector-to-target ratio of 5:1, in the presence of the peptide a the concentrations indicated.

8D. Lysis of HLA-A28 melanoma line by CTL clone LB1801 456/H8.33. Target cells were $^{51}$Cr-labeled and incubated for 4 hours with CTL clone LB1801 456/H8.33 at various effector-to-target ratios.

FIGS. 9A–D. A MAGE-A3 peptide is presented to CTL clone LB1841 526/F7.1 by HLA-B40.

9A. Lysis by CTL clone LB1841 526/F7.1 of autologous EBV-B cells infected with vaccinia-MAGE-A3.

9B. Stimulation of CTL clone LB1841 526/F7.1 by COS-7 cells transiently transfected with a MAGE-A3 cDNA and a cDNA encoding an HLA molecule as indicated.

9C. Lysis by CTL clone LB1841 526/F7.1 of autologous EBV-B cells incubated with synthetic peptide AELVHFLLL (SEQ ID NO: 55) (MAGE-A3$_{114\text{-}122}$).

9D. Lysis of HLA-B40 melanoma cells by CTL clone LB1841 526/F7.1.

FIGS. 10A–D. A MAGE-A1 peptide is presented to CTL clone LB1803 483/G8.4 by HLA-B7.

10A. Lysis by CTL clone LB1803 483/G8.4 of autologous EBV-B cells infected with vaccinia-MAGE-A1.

10B. Stimulation of CTL clone LB1803 483/G8.4 by COS cells transiently transfected with a MAGE-A1 cDNA and a cDNA encoding an HLA molecule as indicated.

10C. Lysis by CTL clone LB1803 483/G8.4 of autologous EBV-B cells incubated with synthetic peptide RVRFFFPSL (SEQ ID NO: 57) (MAGE-A1$_{289\text{-}297}$).

10D. Lysis of HLA-B7 melanoma cells by CTL clone LB1803 483/G8.4.

DETAILED DESCRIPTION OF THE INVENTION

One embodiment of the present invention provides novel methods for isolating CTL clones. The present methods include successive steps of stimulating and testing lymphocytes by using different antigen presenting cells at different steps.

The procedure to develop specific CTL clones in vitro has been described. Briefly, a blood sample containing T-cell precursors is taken from a mammal. PBLs are purified from such blood sample and are incubated with stimulator cells which express antigenic peptides completed with the appropriate MHC molecule. Stimulator cells can be tumor cells (see, e.g., the U.S. Pat. No. 5,342,774, Knuth et al. (Proc. Natl. Acad. Sci. USA 86: 2804–2808, 1989) and Van Den Eynde et al. (Int. J. Cancer 44: 634–640, 1989), or antigen presenting cells pulsed with defined peptides. Additional components, e.g., allogeneic feeder cells and cytokines, can be added into the incubation mixture. CTLs specific for antigens expressed at the surface of the stimulator cells will proliferate, and thus, will be enriched in the cell population as a result of the stimulation. CTL clones can be subsequently isolated by, e.g., limiting dilution. However, the approach using antigen presenting cells pulsed with defined peptides as stimulator cells, have sometimes generated CTLs that are unable to recognize the relevant tumor cells.

The present inventors have found that efficient isolation of CTL clones can be achieved by successive steps of stimulating and testing T cell precursors, using different antigen presenting cells at different steps. The present methods of isolating CTL clones permit significant reduction of CTL activities generated toward non-specific molecules, e.g., molecules expressed from the backbone sequence of an expression vector.

By "different antigen presenting cells" it means that the antigen presenting cells may differ in cell type or in the expression system from which an antigen of interest being presented is derived.

"Antigen presenting cells" as referred herein, express at least one class I or class II MHC determinant and may include those cells which are known as professional antigen-presenting cells such as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used according to the present invention. Examples of facultative antigen-presenting cells include activated T cells, astrocytes, follicular cells, endothelium and fibroblasts. As used herein, "antigen-presenting cells" encompass both professional and facultative types of antigen-presenting cells.

The antigen presenting cells can be isolated from tissue or blood samples (containing peripheral blood mononuclear cells) obtained from a mammal such as human. Cell lines established from such samples may also be used. Procedures for establishing cell lines are well known in the art. Certain cell lines may be obtained directly from the American Type Culture Collection, 10801 University Boulevard, Manassas, Va. 20110-2209. Both normal and malignant cells can be employed.

Preferably, the MHC determinants expressed by the antigen presenting cells are compatible with those expressed by the mammal from which the sample containing T cell precursors is taken. More preferably, autologous antigen presenting cells or cell lines established therefrom are employed. Non-autologous cells may be used as long as the MHC determinants expressed by such cells are compatible, either naturally, by way of transfection or other means that are appropriate. One skilled in the art is also familiar with the methods for determining whether the MHC molecules expressed by an antigen presenting cell are compatible with those of the mammal subject involved, such as well known HLA-typing procedures. See general teachings by Coligan et al. (1994) Current Protocols in Immunology John Wiley & Sons Inc: New York, N.Y.

Preferred antigen presenting cells are autologous dendritic cells, autologous B cells transformed with EBV, and autologous T cell activated by PHA.

Further, according to the present invention, antigen presenting cells used in the present methods can also differ in the expression system from which an antigen of interest is derived. More specifically, the antigen presenting cells can be modified in various ways to effect the expression of an antigen at the cell surface. For example, an antigen presenting cell can be infected with a recombinant Yersinia, a recombinant Salmonella, or a recombinant virus. In each case, the recombinant microorganism encodes a protein from which the peptide antigen presented is derived.

The protein expressed from any of these expression systems is processed in the antigen presenting cells into small peptides, which are then complexed with the appropriate MHC molecules and presented at the cell surface. In the present invention, peptides that are complexed with MHC molecules and presented at the cell surface are also referred to as "antigens".

The term "Yersinia" as used herein includes all species of Yersinia, including *Yersinia enterocolitica, Yersinia pseudotuberculosis* and *Yersinia pestis*. The term "recombinant Yersinia" used herein refers to Yersinia genetically transformed with an expression vector. The term "delivery" used herein refers to the transportation of a protein from a Yersinia to an antigen presenting cell, including the steps of expressing the protein in the Yersinia, secreting the expressed protein(s) from such Yersinia and translocating the secreted protein(s) by such Yersinia into the cytosol of the antigen presenting cell.

According to the present invention, preferred Yersinia for use in expressing and delivering the protein of interest are mutant Yersinia that are deficient in producing functional effector proteins.

A preferred mutant Yersinia strain for use in expressing and delivering the protein of interest is a quintuple-mutant Yersinia strain in which all the effector-encoding genes are mutated such that the resulting Yersinia no longer produce any functional effector proteins. Such quintuple-mutant Yersinia strain is designated as yopEHOMP for *Y. enterocolitica* or yopEHAMJ for *Y. pseudotuberculosis*. One example of such yopEHOMP strain is *Y. enterocolitica* MRS40(pABL403).

An antigenic protein of interest can be cloned into a yersinia expression vector Ffr used in combination with a mutant Yersinia for delivery of the protein into antigen presenting cells. In accordance with the present invention, such a vector is characterized by (in the 5' to 3' direction) a promoter, a first nucleic acid sequence encoding a delivery signal, a second nucleic acid sequence fused thereto coding for the protein to be delivered and other sequences that may be appropriate (e.g., a polyadenylation signal).

The promoter of the expression vector is preferably from a Yersinia virulon gene. A "Yersinia virulon gene" refers to genes on the Yersinia pYV plasmid, the expression of which is controlled both by temperature and by contact with a target cell. See review by Cornelis et al. (1997). Such genes include genes coding for elements of the secretion machinery (the Ysc genes), genes coding for translocators (YopB, YopD, and LcrV), genes coding for the control elements (YopN and LcrG), and genes coding for effectors (YopE, YopH, YopO/YpkA, YopM and YopP/YopJ). Preferably, the promoter is from an effector-encoding gene selected from any one of YopE, YopH, YopO/YpkA, YopM and YopP/YopJ. More preferably, the promoter is from YopE.

Further, in accordance with the present invention, a first DNA sequence coding for a delivery signal is operably linked to the promoter. "A delivery signal", as described hereinabove, refers to a polypeptide which can be recognized by the secretion and translocation system of Yersinia and therefore directs the secretion and translocation of a protein into a an antigen presenting cell. Such polypeptide is from an effector protein including YopE, YpPH, YopO/YpkA, YopM, and YopP/YopJ, and preferably, YopE. More preferably, the effector protein is YopE of *Yersinia enterocolitica*.

One skilled in the art is familiar with the methods for identifying the polypeptide sequences of an effector protein that are capable of delivering a protein. For example, one such method is described by Sory et al. (1994). Examples of such delivery signal polypeptides include from *Y. enterocolitica*: $YopE_{130}$ (the N-terminal 130 amino acids of YopE), $YopE_{50}$, $YopM_{100}$ and $YopH_{71}$.

The yersinia expression vectors may be transformed into Yersinia by a number of known methods which include, but are not limited to, electroporation, calcium phosphate mediated transformation, conjugation, or combinations thereof. For example, a vector can be transformed into a first bacteria strain by a standard electroporation procedure. Subsequently, such a vector can be transferred from the first bacteria strain into Yersinia by conjugation, a process also called "mobilization". Yersinia transformant (i.e., Yersinia having taken up the vector) may be selected, e.g., with antibiotics. These techniques are well known in the art. See, for example, Sory et al. (1994).

The delivery of a protein from a recombinant Yersinia into the cytosol of an antigen presenting cell can be effected by contacting an antigen presenting cell with a recombinant Yersinia under appropriate conditions. Multiple references and techniques are available for those skilled in the art regarding the conditions for inducing the expression and translocation of virulon genes, including the desired temperature, Ca++ concentration, manners in which Yersinia and target cells are mixed, and the like. See, for example, Cornelis, Cross talk between Yersinia and eukaryotic cells, Society for General Microbiology Symposium, 55; Mocrae, Saunders, Smyth, Stow (eds), Molecular aspects of host-pathogen interactions, Cambridge University Press, 1997. The conditions may vary depending on the type of eukaryotic cells to be targeted, e.g.: the conditions for targeting human epithelial carcinoma Hela cells (Sory et al. (1994)); the conditions for targeting mouse thymoma or melanoma cells (Starnbach et al. (1994) *J. Immunol.* 153: 1603); and the conditions for targeting mouse macrophages (Boland et al. (1996)). Such variations can be addressed by those skilled in the art using conventional techniques.

Those skilled in the art can also use a number of assays to determine whether the delivery of a fusion protein is successful. For example, the fusion protein may be labeled with an isotope or an immunofluoresceine, or detected by a immunofluoresceine conjugated antibody, as disclosed by Rosqvist et al. (1994) *EMBO J.* 13: 964. The determination can also be based on the enzymatic activity of the protein being delivered, e.g., the assay described by Sory et al. (1994). The determination can also be based on the antigenicity of the protein being delivered. For example, the delivery of a MAGE-A1 protein into EBV-transformed human B cells can be detected by the recognition of such targeted B cells by CTL cells specific for MAGE-A1 epitopes. Such CTL recognition, in turn, may be detected by a number of assays including assaying the secretion of IFN-γ from the activated CTLs or $Cr^{51}$ release from lysed target cells. Methods such as Western-blot analysis using antibodies specific against the protein being delivered, PCR in situ hybridization, or ELISPOT (Mabtech AB, Sweden) may also be employed for such determination. See, e.g., W. Herr et al. (1997) *J. Immunol. Methods* 203: 141–152 and W. Herr et al. (1996) *J. Immunol. Methods* 191: 131–142.

In accordance with the present invention, the antigenic protein of interest can also be expressed from a recombinant Salmonella. For example, avirulent strains of *Salmonella typhimurium* can be used as antigen delivery vectors. It is known in the art that antigenic epitopes, such as viral epitopes can be successfully delivered to the host cell cytosol by using the type III protein secretion system of *S. typhimurium*. See, e.g., Russmann et al. (1998) 281: 565–568.

In accordance with the present invention, the expression of a protein of interest in the antigen presenting cell can also be effected by infection of the antigen presenting cells with a recombinant virus. In particular, the present invention contemplates recombinant viruses of vaccinia, canarypox virus, other pox viruses, adenovirus, herpes simplex virus, retrovirus and any other viruses that are appropriate.

A preferred strain of vaccinia for use in the present invention is the WR strain (Panicali et al. (1981), *J. Virol.* 37: 1000–1010). The nucleotide sequence coding for the protein of interest can be operably linked to a promoter, such as an vaccinia promoter H6, and inserted into a vaccinia vector, thereby generating a donor plasmid. Vaccinia vectors which can be employed for generating adeno-plasmids are available to those skilled in the art and are described in, e.g., U.S. Pat. No. 4,769,330. Recombinant WR strains of vaccinia can be generated by using a donor plasmid via in vivo recombination, following well-known procedures. See, e.g., Perkins et al., *J. Virol.* 63: 3829–3936 (1989).

A preferred strain of canarypox virus for use in the present invention is ALVAC (Cox et al. (1993), *Virology* 195: 845–850). The nucleotide sequence coding for the protein of interest can be operably linked to a promoter, such as an vaccinia promoter H6, and inserted into an ALVAC vector to create a donor plasmid. Multiple ALVAC vectors are available to one skilled in the art and are described by, e.g., U.S. Pat. No. 5,756,106; Cox et al. (1993) *Virology* 195: 845–850; Tartaglia et al. (1993) *J. Virology* 67: 2370–2375; and Taylor et al. (1992) *Virology* 187: 321–328. Such donor plasmid can be used to generate recombinant ALVAC viruses via in vivo recombination. See, e.g., Cox. et al. (1993); Tartaglia et al. (1993) and Taylor et al. (1992).

Those skilled in the art can also generate recombinant adenoviruses for expressing the protein of interest as described in, e.g., Example 5 hereinafter.

A nucleotide sequence encoding the antigenic protein of interest can be cloned into the various expression vectors as described above. There is no particular limitation in the protein that can be employed in the instant methods for isolating CTL clones.

The term "protein" as used herein refers to naturally occurring proteins as well as artificially engineered proteins, or parts thereof. The term "part of a protein" includes a peptide fragment of a protein that is of sufficient length to be antigenic. Preferably, such a fragment consists of at least 8 or 9 amino acids. "Artificially engineered proteins" as used herein refer to non-naturally occurring proteins, e.g., modified forms of non-naturally occurring proteins, or fusion of two or more naturally occurring proteins or parts thereof, which are also referred to as polytopes (in-frame fusion of two or more epitopes) as exemplified by Thompson et al. (1995) in *Proc. Natl. Acad. Sci. USA* 92: 5845–5849.

The present invention contemplates, in particular, tumor associated proteins or pathogen associated antigens.

A "tumor associated protein" refers to a protein that is specifically expressed in tumors or expressed at an abnormal level in tumors relative to normal tissues. Such tumor associated proteins include, but are not limited to, members of the MAGE family, the BAGE family (such as BAGE-1), the DAGE/PRAME family (such as DAGE-1), the GAGE family, the RAGE family (such as RAGE-1), the SMAGE family, NAG, Tyrosinase, Melan-A/MART-1, gp100, MUC-1, TAG-72, CA125, mutated proto-oncogenes such as p21ras, mutated tumor suppressor genes such as p53, tumor associated viral antigens (e.g., HPV16 E7), the SSX family, HOM-MEL-55, NY-COL-2, HOM-HD-397, HOM-RCC-1.14, HOM-HD-21, HOM-NSCLC-11, HOM-MEL-2.4, HOM-TES-11, RCC-3.1.3, NY-ESO-1, and the SCP family. Members of the MAGE family include, but are not limited to, MAGE-A1, MAGE-A2, MAGE-A3, MAGE-A4, MAGE-A11. Members of the GAGE family include, but are not limited to, GAGE-1, GAGE-6. See, e.g., review by Van den Eynde and van der Bruggen (1997) in *Curr. Opin. Immunol.* 9: 684–693, Sahin et al. (1997) in *Curr. Opin. Immunol.* 9: 709–716, and Shawler et al. (1997). These proteins have been shown to associate with certain tumors such as melanoma, lung cancer, prostate cancer, breast cancer, renal cancer and others.

A number of known antigenic proteins from pathogens are also contemplated by the present invention.

The pathogens can include viruses, bacteria, parasites and fungi. Specific examples of antigenic proteins characteristic of a pathogen include the influenza virus nucleoprotein (residues 218–226, as set forth in F. et al. (1997) *J. Virol.* 71: 2715–2721) antigens from Sendai virus and lymphocytic choriomeningitis virus (see, An et al. (1997) *J. Virol.* 71: 2292–2302), the B1 protein of hepatitis C virus (Bruna-Romero et al. (1997) *Hepatology* 25: 470–477), the virus envelope glycoprotein gp 160 of HIV (Achour et al. (1996) *J. Virol.* 70: 6741–6750), amino acids 252–260 or the circumsporozite protein of *Plasmodium berghei* (Allsopp et al. (1996) *Eur. J. Immunol.* 26: 1951–1958), the influenza A virus nucleoprotein (residues 366–374, Nomura et al. (1996) *J. Immunol. Methods* 193: 4149), the listeriolysin O protein of *Listeria monocytogenes* (residues 91–99, An et al. (1996) *Infect. Immun.* 64: 1685–1693), the E6 protein (residues 131–140, Gao et al. (1995) *J. Immunol.* 155: 5519–5526) and E7 protein (residues 21–28 and 48–55, Bauer et al. (1995) *Scand. J. Immunol.* 42: 317–323) of human papillomavirus type 16, the M2 protein of respiratory syncytial virus (residues 82–90 and 81–95, Hsu et al. (1995) *Immunology* 85: 347–350), the herpes simplex virus type 1 ribonucleotide reductase (see, Salvucci et al. 1995) *J. Gen. Virol.* 69: 1122–1131) and the rotavirus VP7 protein (see, Franco et al. (1993) *J. Gen. Virol.* 74: 2579–2586), *P. falciparum* antigens (causing malaria) and hepatitis B surface antigen (Gilbert et al. (1997) *Nature Biotech.* 15: 1280–1283).

A number of short antigenic peptides can also be employed in the present invention. One skilled in the art can readily determine the length of the fragments required to produce immunogenic peptides. Alternatively, the skilled artisan can also use coding sequences for peptides that are known to elicit specific T cell responses (either CD4+ or CD8+ T cells), such as tumor-associated antigenic peptides (TAA, also known as TRAs for tumor rejection antigens) as disclosed by U.S. Pat. Nos. 5,462,871, 5,558,995, 5,554, 724, 5,585,461, 5,591,430, 5,554,506, 5,487,974, 5,530,096, 5,519,117. Examples of TRAs are provided in Table 1. See also review by Van den Eynde and van der Bruggen (1997) and Shawler et al. (1997). Antigenic peptides of a pathogen origin can also be used, such as those disclosed by Gilbert et al. (1997).

TABLE 1

Exemplary Antigens

| Gene | MHC | Peptide | Position | SEQ ID NO: |
|---|---|---|---|---|
| MAGE-A1 | HLA-A1 | EADPTGHSY | 161–169 | 1 |
|  | HLA-Cw16 | SAYGEPRKL | 230–238 | 2 |
| MAGE-A3 | HLA-A1 | EVDPIGHLY | 168–176 | 3 |
|  | HLA-A2 | FLWGPRALV | 271–279 | 4 |
|  | HLA-B44 | MEVDPIGHLY | 167–176 | 5 |
| BAGE | HLA-Cw16 | AARAVFLAL | 2–10 | 6 |
| GAGE-1,2 | HLA-Cw16 | YRPRPRRY | 9–16 | 7 |
| RAGE | HLA-B7 | SPSSNRIRNT | 11–20 | 8 |

TABLE 1-continued

Exemplary Antigens

| Gene | MHC | Peptide | Position | SEQ ID NO: |
|---|---|---|---|---|
| GnT-V | HLA-A2 | VLPDVFIRC(V) | 2–10/11 | 9 |
| MUM-1 | HLA-B44 | EEKLIVVLF | exon 2/ intron | 10 |
|  |  | EEKLSVVLF (wild type) |  | 11 |
| CDK4 | HLA-A2 | ACDPHSGHFV | 23–32 | 12 |
|  |  | ARDPHSGHFV (wild type) |  | 13 |
| β-catenin | HLA-A24 | SYLDSGIHF | 29–37 | 14 |
|  |  | SYLDSGIHS (wild type) |  | 15 |
| Tyrosinase | HLA-A2 | MLLAVLYCL | 1–9 | 16 |
|  | HLA-A2 | YMNGTMSQV | 369–377 | 17 |
|  | HLA-A2 | YMDGTMSQV | 369–377 | 18 |
|  | HLA-A24 | AFLPWHRLF | 206–214 | 19 |
|  | HLA-B44 | SEIWRDIDF | 192–200 | 20 |
|  | HLA-B44 | YEIWRDIDF | 192–200 | 21 |
|  | HLA-DR4 | QNILLSNAPLGPQFP | 56–70 | 22 |
|  | HLA-DR4 | DYSYLQDSDPDSFQD | 448–462 | 23 |
| Melan-A$^{MART-1}$ | HLA-A2 | (E)AAGIGILTV | 26/27–35 | 24 |
|  | HLA-A2 | ILTVILGVL | 32–40 | 25 |
| gp-100$^{Pme1117}$ | HLA-A2 | KTWGQYWQV | 154–162 | 26 |
|  | HLA-A2 | ITDQVPFSV | 209–217 | 27 |
|  | HLA-A2 | YLEPGPVTA | 280–288 | 28 |
|  | HLA-A2 | LLDGTATLRL | 457–466 | 29 |
|  | HLA-A2 | VLYRYGSFSV | 476–485 | 30 |
| DAGE | HLA-A24 | LYVDSLFFL | 301–309 | 31 |
| MAGE-A6 | HLA-Cw16 | KISGGPRISYPL | 292–303 | 32 |

As described herein above, sequences coding for a full-length naturally occurring protein, a part of a naturally occurring protein, combinations of parts of a naturally occurring protein, or combinations of different naturally occurring proteins or parts from different proteins, may all be employed to be cloned into the expression vectors as described hereinabove.

The present invention further provides recombinant expression vectors which can be employed in the present methods, including recombinant yersinia expression vectors, e.g., pMS111-YopE$_{130}$-MAGE-A1 and PMS111-YopE$_{130}$-MAGE-A4; recombinant vaccinia vectors, e.g., WR-MAGE-A1 and WR-MAGE-A4; recombinant canary-pox viral vectors, e.g., ALVAC-MAGE-A1; recombinant adenoviral vectors, e.g., adeno-MAGE-A4; and retroviral vectors, e.g., M1-CSM.

To carry out the methods of the present invention, a sample containing T-cell precursors is obtained from a subject, typically, a blood sample from a human subject. The subject can be a cancer patient or an individual without cancer. The sample may be treated to concentrate T-cell precursors prior to stimulation.

The sample is contacted with a first antigen presenting cell expressing a protein, along with any other materials that may be appropriate, such as lymphokines. Upon contact, specific T-cell precursors are activated and begin to proliferate.

Cells in the sample are subsequently tested by contacting the cells with a second antigen presenting cell expressing the protein. The sample can be first diluted and distributed into microwells such that individual cells can be separately tested. CTL Cells which are specific for the protein, or "responding CTLs", can be identified and selected by a variety of standard assays such as a $^{51}$Cr release assay, a IFN-γ secretion assay, or a TNF production assay.

In a preferred embodiment of the present invention, the CTL cells thus selected are subject to at least one additional cycle of stimulation and testing steps.

According to the present invention, the antigen presenting cells used at one step can differ from the cells used in a subsequent step, either in cell type or in the expression system from which the protein is expressed.

For testing the specificity of CTL responses after stimulation, antigen presenting cells of a type that expresses high amounts of class I HLA molecules are preferred, e.g., EBV-transformed B cells.

In a preferred embodiment of the present invention, one of the expression systems used by the antigen presenting cell at one step (either stimulation or testing), is different from at least one of the other expression systems used in another step.

More Preferably, the antigen presenting cells used at a stimulation step employ an expression system different from that used in the immediately following testing step.

The present invention provides examples of combinations of different antigen presenting cells which can be used for isolating specific CTL clones. According to the present invention, CD8$^+$ T lymphocytes obtained from an individual can be stimulated in microwells with autologous monocyte-derived dendritic cells infected with a recombinant ALVAC canarypoxvirus encoding a protein of interest. After several times of stimulation, an aliquot of each microculture can then be tested for specific lysis of autologous EBV-B cells infected with a recombinant Vaccinia encoding the protein of interest. The positive microcultures can then be diluted and stimulated again with autologous EBV-B cells infected with a recombinant Yersinia encoding the protein of interest. Specific clones can be detected and thus isolated by testing for specific lysis of autologous EBV-B cells infected with a recombinant Vaccinia encoding the protein of interest. Thus, the combination of antigen presenting cells used in the foregoing procedure can be characterized as dendritic-ALVAC/EBV-B-Vaccinia/EBV-B-Yersinia/EBV-B-Vaccinia. Additional preferred combinations of antigen presenting cells which can be used in the present methods include: dendritic-Adeno/EBV-B-Vaccinia/EBV-B-Yersinia/EBV-B-Vaccinia, dendritic-ALVAC/EBV-B-Vaccinia/T cell-retroviral/EBV-B-Vaccinia. The present invention is not limited to the above exemplified combinations.

In a further aspect of the invention, the present invention contemplates CTL clones isolated by using the methods of the present invention.

In another embodiment, the present invention contemplates methods for identifying antigenic peptide epitopes of a protein. According to such method, CTL clones that recognize certain antigenic epitopes of a protein are isolated using the present method of isolating CTL clones, as described hereinabove. Such clones can then be used to identify the specific antigenic peptides as well as the presenting HLA molecules, using a variety of well-known procedures, for example, procedures described in Examples 7–11.

According to the methods of the present invention, the identification of an antigenic peptide epitope of a protein is based on the capacity of the peptide/HLA complex, at the surface of an antigen presenting cell, to activate the specific CTLs. The antigenic peptide epitopes thus identified likely represent the epitopes that are well processed and adequately expressed at the cell surface in vivo. By using such method of the present invention, antigenic peptide epitopes from proteins of the MAGE family have been identified; namely, MAGE-A1 peptide 230–238 (presented by HLA-Cw3 and recognized by clone LB1137 462/F3.2), MAGE-A1 peptide 258–266 (presented by HLA-B53 and recognized by clone LB1801 456/H7.11), MAGE-A1 peptide 62–70 (presented by HLA-Cw2 and recognized by clone LB 1118 466/D3.31), MAGE-A1 peptide 222–231 (presented by HLA-A28 and recognized by clone LB1801 456/H8.33), MAGE-A1 peptide 289–297 (presented by HLA-B7 and recognized by clone LB1803 483/G8.4), a MAGE-A3 peptide 114–122 (presented by HLA-B40 and recognized by clone LB1841 526/F7.1), and a MAGE-A4 peptide 230–239 (presented by HLA-A2 and recognized by clone LB1137 H4.13). See Table 2. Among these, MAGE-A1 peptide 230–238 (SAYGEPRKL (SEQ ID NO: 2)) has been previously identified, but was found therein to be presented by a different HLA molecule, HLA-Cw16 (U.S. Pat. No. 5,558,995).

TABLE 2

| GENE | POSITION | PEPTIDE | MHC | CTL | SEQ ID |
|---|---|---|---|---|---|
| MAGE-A1 | 230–238 | SAYGEPRKL | HLA-Cw3 | LB1137 462/F3.2 | 2 |
| MAGE-A1 | 258–266 | DPARYEFLW | HLA-B53 | LB1801 456/H7.11 | 42 |
| MAGE-A4 | 230–239 | GVYDGREHTV | HLA-A2 | LB1137 H4.13 | 44 |
| MAGE-A1 | 62–70 | SAFPTTINF | HLA-Cw2 | LB1118 466/D3.31 | 47 |
| MAGE-A1 | 222–231 | EVYDGREHSA | HLA-A28 | LB1801 456/H8.33 | 48 |
| MAGE-A3 | 114–122 | AELVHFLLL | HLA-B40 | LB1841 526/F7.1 | 55 |
| MAGE-A1 | 289–297 | RVRFFFPSL | HLA-B7 | LB1803 483/G8.4 | 57 |

Accordingly, another embodiment of the present invention provides isolated CTL clones that are specific for peptide/HLA complexes SAYGEPRKL(SEQ ID NO: 2)/HLA-Cw3, DPARYEFLW(SEQ ID NO: 42)/HLA-B53, GVYDGREHTV(SEQ ID NO: 44)/HLA-A2, SAFPTTINF (SEQ ID NO: 47)/HLA-Cw2, EVYDGREHSA(SEQ ID NO: 48)/HLA-A28, AELVHFLLL(SEQ ID NO: 55)/HLA-B40, and RVRFFFPSL(SEQ ID NO: 57)/HLA-B7, respectively.

In a preferred embodiment, the present invention provides isolated CTL clones LB1137 462/F3.2, LB1801 456/H7.11, LB1118 466/D3.31, LB1801 456/H8.33, LB1137 H4.13, LB1841 526/F7.1 and LB1803 483/G8.4.

In another embodiment, the present invention is directed to the newly isolated antigenic peptides, namely, DPARYEFLW(SEQ ID NO: 42) (MAGE-A1 258–266), GVYDGREHTV(SEQ ID NO: 44) (MAGE-A4 230–239), SAFPTTINF(SEQ ID NO: 47) (MAGE-A1 62–70), EVYDGREHSA(SEQ ID NO: 48) (MAGE-A1 222–231), AELVHFLLL (SEQ ID NO: 55) (MAGE-A3 114–122) and RVRFFFPSL (SEQ ID NO: 57) (MAGE-A1 289–297). Nucleic acid sequences encoding these peptides are also contemplated.

Another embodiment of the present invention is directed to the isolated peptide/HLA complexes of the present invention. Specifically, the present invention provides isolated complex of peptide SAYGEPRKL(SEQ ID NO: 2) and HLA-Cw3, complex of peptide DPARYEFLW(SEQ ID NO: 42) and HLA-B53, complex of peptide GVYDGREHTV (SEQ ID NO: 44) and HLA-A2, complex of peptide SAFPTTINF(SEQ ID NO: 47) and HLA-Cw2, complex of peptide EVYDGREHSA(SEQ ID NO: 48) and HLA-A28, complex of AELVHFLLL (SEQ ID NO: 55) and HLA-B40, and complex of RVRFFFPSL (SEQ ID NO: 57) and HLA-B7.

Once the presenting HLA molecule for an antigenic peptide epitope has been ascertained, a complex of the peptide and the HLA molecule can be made by a variety of methods. For example, the HLA molecule can be produced and isolated by any appropriate recombinant expression system, e.g., an *E. coli*-based expression system. Peptides can be made by, e.g., chemical synthesis or recombinant expression. The peptides and the HLA molecules can then be mixed in vitro under conditions that favor the formation of the HLA/peptide complexes. Such conditions are well known in the art. See, e.g., Garboczi et al. (*Proc. Natl. Acad. Sci. USA* 89: 3429–3433, 1992 and Altman et al. (*Science* 274: 94–96, 1996).

The present invention further contemplates cells expressing any of the instant peptide/HLA complexes at the cell surface. Such cells can be made using any antigen presenting cells that are appropriate including cell lines (e.g., COS cells, CHO cells and the like), and by, e.g., peptide loading, or cotransfection as described in the Examples of the present disclosure.

In another embodiment, the present invention contemplates pharmaceutical compositions which include any one of the isolated CTL clones, the isolated antigenic peptides, the isolated peptide/HLA complexes, the antigen presenting cells expressing peptide/HLA complexes of the present invention, or combinations thereof.

The pharmaceutical compositions of the present invention can include other substances such as cytokines, adjuvants and pharmaceutically acceptable carriers. As used herein, a therapeutically acceptable carrier includes any and all solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art. Supplementary active ingredients can also be incorporated into the compositions.

In a further aspect of the present invention, the isolated CTL clones, the isolated antigenic peptides, the cells expressing the peptide/HLA complexes of the present invention are employed in various methods for diagnosing a pathological condition in a subject, preferably, a human subject.

The pathological conditions contemplated by the present invention include tumors and infections by pathogens such as bacteria, parasites, fungus or virus, and the like.

The term "abnormal expression" as used herein refers to an expression that is not present in normal cells or an expression that is present in normal cells at a significantly lower level. In the present invention, "an abnormal expression" can also be used to refer to an unusual processing of a protein which gives rise to an antigenic epitope that is not presented at the surface of normal cells.

In one embodiment, the present invention provides methods of diagnosing in a subject, a pathological condition characterized by an abnormal expression a peptide/HLA complex, by detecting in the subject, the presence of cells abnormally expressing such complex.

In another embodiment, the present invention provides methods of detecting in a subject the presence of cells abnormally expressing a peptide/HLA complex of the present invention, by using an isolated CTL clone specific for such complex.

According to the present invention, a sample containing the cells suspected to be abnormal is obtained from the subject by, e.g., tissue biopsy. The sample is then contacted with a CTL clone of the present invention. The presence of the abnormal cells can be determined by measuring the activity of the CTL clone (i.e., CTL response) using standard assays such as $^{51}$Cr release, IFN-gamma secretion, or TNF production.

In another embodiment, the present invention provides methods for detecting in a subject, the presence of CTL cells specific for an isolated peptide/HLA complex of the present invention. More specifically, a blood sample is secured from the subject and contacted with cells expressing the specific peptide/HLA complexes. The presence of CTL cells specific for the complex can be detected by any of the approaches described hereinabove, e.g., the lysis of the cells expressing the specific peptide/HLA complexes measurable by a standard $^{51}$Cr release assay.

Furthermore, the frequency of CTLs specific for a peptide/HLA complex can be assessed by, e.g., limiting dilution analysis or tetramer assays. By comparing with a normal individual, an increased frequency of CTLs specific for a peptide/HLA complex in an individual, is indicative of a pathological condition characterized by an abnormal expression of the complex. Accordingly, the present invention contemplates methods of diagnosing a pathological condition characterized by an abnormal expression of a peptide/HLA complex by detecting an increased frequency of CTLs specific for such peptide/HLA complex.

In a further aspect of the present invention, the isolated CTL clones, the isolated antigenic peptides, the cells expressing the peptide/HLA complexes of the present invention are employed in various methods for treating a pathological condition in a subject, preferably, a human subject.

The term "treating" is used to refer to alleviating or inhibiting a pathological condition, e.g., inhibiting tumor growth or metastasis, reducing the size of a tumor, or diminishing symptoms of a pathogen infection, by e.g., eliciting an immune response.

In one embodiment, an isolated CTL clone of the present invention can be administered, in a therapy regimen of adoptive transfer, to a subject suffering a pathological condition characterized by an abnormal expression of the peptide/HLA complex that is specifically recognized by such CTL clone. See teachings by Greenberg (1986) *J. Immunol.* 136 (5): 1917; Riddel et al. (1992) Science 257: 238; Lynch et al. (1991) *Eur. J. Immunol.* 21: 1403; and Kast et al. (1989) *Cell* 59: 603 for adoptive transfer. CTLs, by lysing the cells abnormally expressing such antigens, can alleviate or treat the pathological condition at issue, such as a tumor and an infection with a parasite or a virus.

In another embodiment, the present invention provides methods of treating a subject suffering a pathological condition characterized by an abnormal expression of a peptide/HLA complex, by administering the isolated peptides, or the peptide/HLA complexes, to the subject. The pathological condition can be alleviated by, e.g., specific immune responses elicited due to the administered peptides or peptide/HLA complexes.

In another embodiment of the present invention, a subject suffering a pathological condition characterized by an abnormal expression of a peptide/HLA complex of the present invention, can be treated by obtaining antigen presenting cells from the subject, modifying such cells to effect a presentation of the peptide/HLA complex at the cell surface, and then reperfusing such "loaded" cells into the subject.

The modification can be achieved by transfecting the isolated antigen presenting cells with any appropriate expression vectors encoding the peptide or the full-length protein, or by loading the cells with the peptides at issue following a peptide loading procedure as described by, e.g., Nestle et al. (*Nature Medicine* 4: 328–332, 1998).

For treatment purposes, the isolated CTL clones, the peptides or the peptide/HLA complexes, or the cells expressing the peptide/HLA complexes, can be administered to a subject alone or in combination with other appropriate materials, such as cytokines, adjuvants or a pharmaceutical carriers. The amount of the CTL cells, the peptides, the peptide/HLA complexes, or cells expressing the complexes, can be determined according the condition of the subject.

For additional teachings of diagnostic and therapeutic uses of isolated CTLs and peptide/HLA complexes, see, e.g., Thomson et al. (1995) PNAS 92: 5845; Altman et al. (1996) *Science* 274: 94–96; Dunbar et al. (1998) *Current Biology* 8: 413–416; Greenberg et al. (1986) *J. Immunol.* 136: 1917; and Kast et al. (1989) *Cell* 59: 603–614.

The present invention is further illustrated by the following examples.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, recognizing that various modifications are possible within the scope of the invention.

EXAMPLE 1

Generation of Recombinant Yersinia and Targeting EBV-Transformed B Cells with Recombinant Yersinia Strains, Plasmids and Growth Conditions

*Y. enterocolitica* strain E40(pYV40), MRS40(pYV40), which is the isogeneic ampicillin sensitive derivative of E40(pYV40), and their various non-polar mutants (Sory et al. (1995), *Proc. Natl Acad. Sci. USA* 92: 11998–12002). Plasmids are listed in Table 3. Bacteria were grown in Brain Heart Infusion (BHI) (Difco, Detroit, Mich.). After overnight preculture, bacteria were diluted 1/20 in fresh BHI, allowed to grow for 30 minutes at room temperature, and synthesis of the Yop virulon was induced by incubation for 150 minutes at 37° C. before infection.

Construction of the Polymutant Yersinia Strains

To construct the yopHOPEM polymutant strain, the yopE, yopH, yopo, yopM and yopP genes were successively knocked out by allelic exchange in the MRS40 strain using the suicide vectors pMRS101 and pKNG101. See, K. Kaniga et al. (1991) "A wide-host range suicide vector for improving reverse genetics in gram-negative bacteria: inactivation of the blaA gene of Yersinia enterocolitica" *Gene* 109: 137–141 and M. R. Sarker et al. (1997) "An improved version of suicide vector pKNG101 for gene replacement in Gram-negative bacteria" *Mol. Microbiol.* 23: 409–411. The various deletions are described in Table 2 in the "suicide vectors and mutators" section. The YopE gene was first mutated using the mutator pPW52 (see, P. Wattiau et al. (1993) "SycE, a chaperone-like protein of *Yersinia enterocolitica* involved in the secretion of YopE" *Mol. Microbiol.* 8: 123–131), giving strain MRS40(pAB4052). Mutation of the YopH gene in this strain with the mutator pAB31 (see, S. D. Mills et al. (1997) "*Yersinia enterocolitica* induces apoptosis in macrophages by a process requiring functional type III secretion and translocation mechanisms and involving YopP, presumably acting as an effector protein" *Proc. Natl. Acad. Sci. USA* 94: 12638–12643) gave the double yopEH mutant MRS40(pAB404). The triple yopEHO mutant MRS40(pAB405) was then obtained by allelic exchange with the mutator pAB34 (see, S. D. Mills et al., 1997). The YopP gene was then mutated with mutator pMSK7 (see S. D. Mills et al. (1997)), leading to the yopEHOP mutant MRS40(pMSK46). The yopHOPEM strain MRS40(pABL403) was finally obtained by allelic exchange with the yopM mutator pAB38 (see, S. D. Mills et al., 1997).

TABLE 3

Plasmids

| Plasmids | Relevant Characteristics | References |
|---|---|---|
| pABL403 | pYV40 yopE$_{21}$, yopHΔ$^{1-352}$ yopOΔ$^{65-558}$, yopP$_{23}$, yopM$_{23}$ Suicide Vectors and mutators | see Example 2 of the present specification |
| pKNG101 | $^{ori}$R6K $^{aac}$BR+ $^{on}$TRK2 $^{str}$AB+ | K. Kaniga et al. (1991) Gene 109: 137–141. |
| pMRS101 | $^{ori}$R6K $^{sac}$BR+ $^{on}$TRK2 $^{str}$AB+ $^{ori}$ColE1 bla + | M.R. Sarker and G.R. Cornelis (1997) Mol. Microbiol. 23: 409–411. |
| pAB31 | pMRS101 yopHΔ$_{1-352}$+ | S.D. Mills et al. (1997) Proc. Natl. Acad. Sci. USA 94: 12638–12643. |
| pAB34 | pMRS101 yopOΔ$_{65-558}$+ | S.D. Mills et al. (1997) |
| pAB38 | pMRS101 yopM$_{23}$+ | S.D. Mills et al. (1997) |
| pMSK7 | pMRS101 yopP$_{23}$+ | S.D. Mills et al. (1997) |
| pPW52 | pKNG101 yopE$_{21}$+ | P. Wattiau and G.R. Cornelis (1993) Mol. Microbiol. 8: 123–131. |

Generation of recombinant Yersinia containing YopE$_{130}$-MAGE-A1

The sequence encoding protein MAGE-A1 was inserted in frame with a sequence encoding a truncated YopE, $YopE_{130}$, containing the first 130 amino acids of YopE. Such a plasmid is graphically depicted in FIG. 1.

The open reading frame of MAGE-A1 was amplified by PCR using a MAGE-A1 cDNA cloned in pcDNAI/Amp (Invitrogen, Carlsbad, Calif.) as template. The upstream primer, AAACTGCAGATGTCTCTTGAGCAGAGGAGTC (SEQ ID NO: 33), consisted of the first nucleotides of the open reading frame of MAGE-A1 preceded by a PstI site. The downstream primer, AAACTGCAGTCAGACTCCCTCTTCCTCCTC (SEQ ID NO: 34), consisted of nucleotides complementary to the last nucleotides of the open reading frame of MAGE-A1 followed by a PstI site. The PCR product was digested with PstI and inserted in frame with the truncated YopE at the PstI site of vector pMS111 (see, Sory et al. (1994) *Molecular Microbiology* 14: 583–594), to yield plasmid $YopE_{130}$-MAGE-A1 or pMS111-MAGE-A1.

pMS111-MAGE-A1 ($YopE_{130}$-MAGE-A1) was electroporated in bacteria strain DH5 F'IQ. DNA was extracted from some clones and the DNA of a positive recombinant clone was electroporated in bacteria strain SM10. After mobilization of pMS111 from SM10 in Yersinia MRS40 (pABL403), recombinant clones were then selected on agar-containing medium, supplemented with nalidixic acid, sodium-arsenite and chloramphenicol. MRS40 is an isogeneic derivative of E40 sensitive to ampicillin (see, Sory et al. (1995) *Proc. Natl. Acad. Sci. USA* 92: 11998–12002).

Generation of recombinant Yersinia containing $YopE_{130}$-MAGE-A4

The sequence encoding protein MAGE-A4 was linked in frame to a sequence encoding a truncated YopE, YopE (1–130), containing the first 130 amino acids of YopE. The open reading frame of MAGE-A4 was amplified by PCR using a MAGE-A4 cDNA cloned in pcDNAI/Amp (Invitrogen) as template. The upstream primer, AAAAACTGCAGATGTCTTCTGAGCAGAAGAGT (SEQ ID NO: 35), consisted of the first nucleotides of the open reading frame of MAGE-A4 preceded by a PstI site. The downstream primer, AAAAAATCGATTCAGACTCCCTCTTCCTC (SEQ ID NO: 36), consisted of nucleotides complementary to the last nucleotides of the open reading frame of MAGE-A4 followed by a ClaI site. The PCR was performed for 30 cycles (1 min at 94° C., 2 min at 55° C. and 2 min at 72° C.). The PCR product was digested with PstI and ClaI and inserted in frame with the truncated YopE at the PstI-ClaI sites of vector pMS621. Plasmid pMS621-MAGE-A4 was transformed into bacteria strain DH5αF'IQ by electroporation. Positive clones were detected by PCR on bacterial colonies and the DNA of a positive recombinant clone was extracted and transformed into bacteria strain SM10 by electroporation. After mobilization of pMS621-MAGE-A4 from SM10 into polymutant Yersinia MRS40 (pABL403), recombinant clones were then selected on agar-containing medium, supplemented with nalidixic acid, sodium m-arsenite and chloramphenicol.

Generation of recombinant Yersinia-MAGE-A3

Yersinia-MAGE-A3(aa147–314)

The sequences encoding the truncated MAGE-A3 was amplified by PCR using a MAGE-A3 cDNA cloned in pcDNAI/Amp as template. The upstream primer PVB157 was 5'-AA CTGCAG TTTCCTGTGATCTTCAGCAAAGC-3'(SEQ ID NO: 50), consisting of nucleotides 439–461 of the open reading frame of MAGE-A3 (start codon ATG is 1–3), preceded by a PstI site (in bold) and 2 A's. The downstream primer PVB139, 5'-CC ATCGAT TCACTCTTCCCCCTCTCTCAA-3'(SEQ ID NO: 51), consisting of nucleotides complementary to the last nucleotides of the open reading frame of MAGE-A3 preceded by a ClaI site (in bold) and 2C's. PCR was performed for 30 cycles (1 min at 94° C., 2 min at 62° C. and 2 min at 72° C.). The PCR products were treated as described for MAGE-A4 hereinabove.

Construction of yersinia-MAGE-A3(aa1–199)

To obtain the sequence encoding the first 199 amino-acids of the MAGE-A3 protein, the primers were designed as follows: upstream primer PVB172, 5'-ACCAGAGTCATC CTGCAG <u>ATG</u>CCTCTTGAG -3' (SEQ ID NO: 52), consisting of the nucleotides overlapping the start codon (underlined) of the open reading frame of MAGE-A3 preceded by a PstI site (in bold). The downstream primer PVB 173, 5'-GCCTGCCTTGGG ATCGAT TCACATGATCTGATT-3'(SEQ ID NO: 53), consisting of nucleotides complementary to the nucleotides 577–600 of the open reading frame of MAGE-A3 and containing a ClaI site (in bold). PCR was performed for 30 cycles (1 min at 94° C., 2 min at 65° C. and 2 min at 72° C.). The PCR products were treated as described hereinabove for MAGE-A4.

Targeting EBV-Transformed B Cells with Recombinant Yersinia

Infection of EBV-transformed B cells with Yersinia MRS40 (pABL403) containing pMS111-MAGE-A1 was carried out as follows. Infection of EBV-transformed B cells with other recombinant Yersinia was carried out following essentially the same procedure.

One colony of Yersinia MRS40 (pABL403) containing pMS111-MAGE-A1 was then grown overnight at 28° C. in LB medium supplemented with nalidixic acid (35 μg/ml), sodium m-arsenite (1 mM) and chloramphenicol (12 µg/ml). The overnight culture was diluted in fresh medium in order to obtain an OD (optical density) of 0.2 at 600 nm after amplifying the fresh culture at 28° C. for approximately 2 hours. The bacteria were washed in 0.9% NaCl and resuspended at $10^8$ bacteria per ml in 0.9% NaCl assuming that a culture giving an $OD_{600}$ equal to 1 contains $5 \times 10^8$ bacteria per ml. Irradiated EBV-B cells (100 Gy) were resuspended at $10^6$ in 3.8 ml of RPMI without antibiotics, supplemented with 10% FCS and AAG (L-Arginine (116 mg/ml), L-Asparagine (36 mg/ml) and L-Glutamine (216 mg/ml)). Then 200 µl of the bacterial suspension was added. Two hours after infection, gentamicin (30 µg/ml) was added for the nest two hours, and the cells were finally washed three times before being used as stimulator cells.

As a negative control, the same cells were also infected with Yersinia MRS40 (pABL403) containing pMS621, a plasmid which encodes only the truncated YopE, i.e., $YopE_{130}$.

Figure 2A:
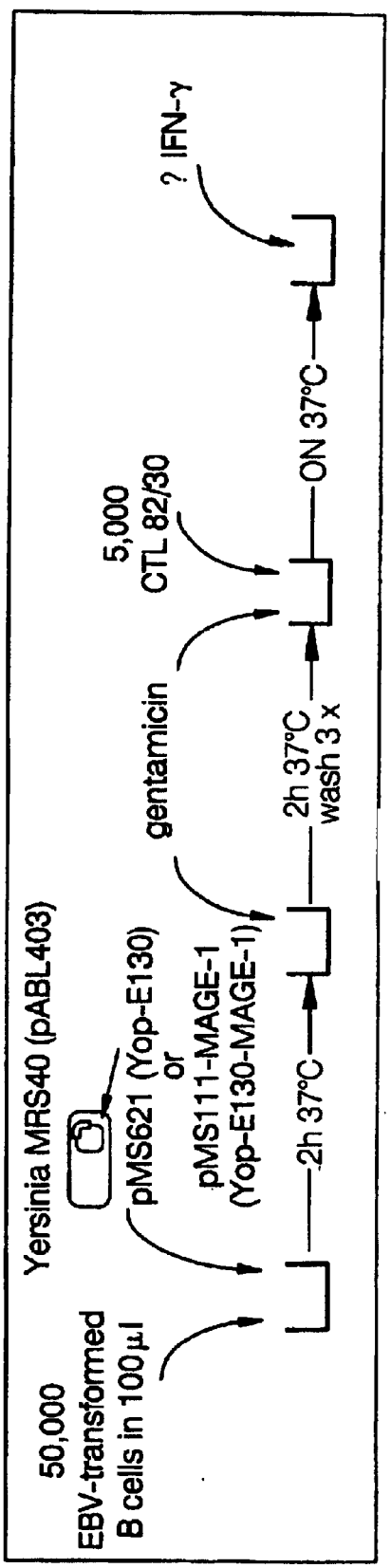
FIGS. 2A–2B depicts the procedure for stimulating CTL 82/30 with EBV-transformed human B cells (HLA-A1) mixed with recombinant Yersinia.

EBV-B Cells infected with the recombinant Yersinia-MAGE-A1 were recognized by MZ2-CTL 82/30. MZ2-CTL 82/30 are specific for the MAGE-A1 peptide EADPTGHSY (SEQ ID NO: 1) which is presented by HLA-A1 (U.S. Pat. No. 5,342,774). 5000 MZ2-CTL 82/30 cells were added in each microwell containing the Yersinia in a final volume of 100 µl of Iscove's complete medium (culture medium was supplemented with 10% human serum, L-arginine (116 mg/ml), L-asparagine (36 mg/ml), L-glutamine (216 mg/ml), streptomycine (0.1 mg/ml), penicillin (200 U/ml), IL-2 (25 U/ml) and gentamicin (15 µg/ml). After overnight incubation, the presence of IFN-gamma (that is produced by CTL upon activation) in the supernatant of the co-culture was tested in a standard ELISA assay (Biosource, Fleurus, Belgium). FIG. 2A graphically depicts such a procedure.

Figure 2B:
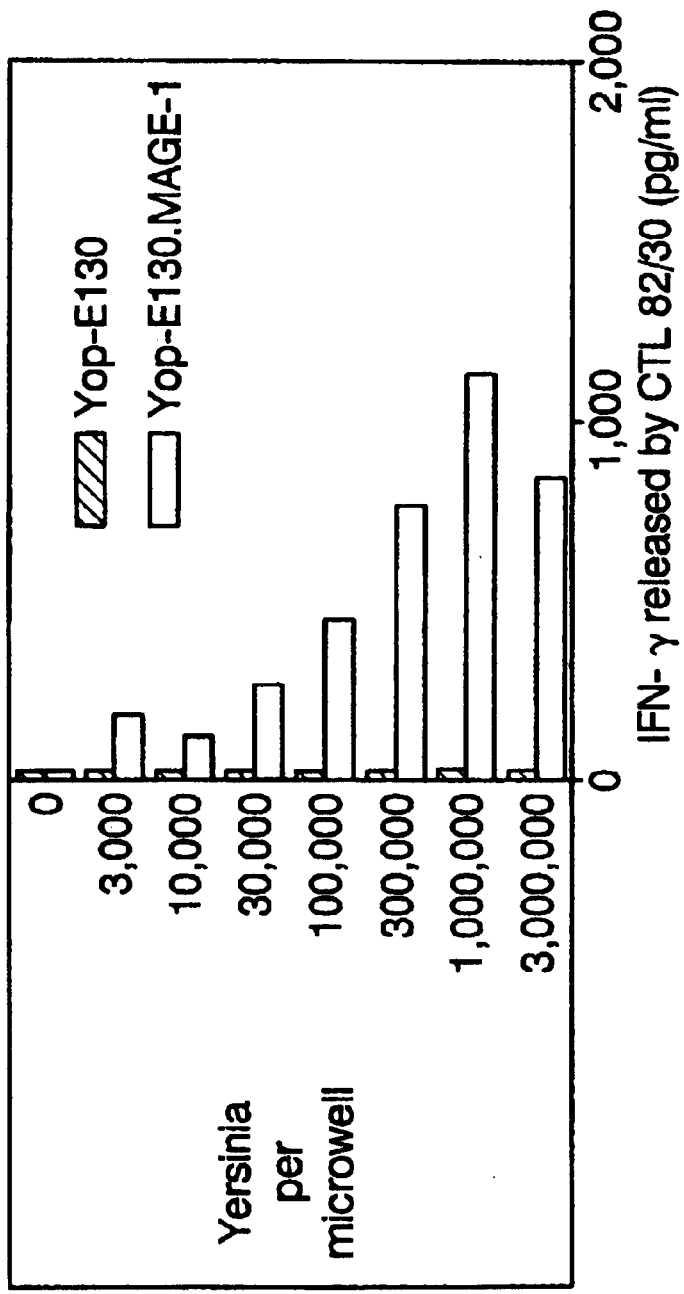

As indicated in FIG. 2B, the HLA-A1$^+$ B cells infected with Yersinia encoding $YopE_{130}$-MAGE-A1 were recognized by the CTL 82/30, while the same cells infected with the control plasmid $YopE_{130}$ were not. The optimal concentration of bacteria is around 1,000,000 per microwell.

EXAMPLE 2

Generation of Recombinant Vaccinia WR Viruses

Parental WR strain of Vaccinia (vP1170) contained the parent vector pKILGPT of 2826 bp (Virogenetics, Troy, N.Y.). A sequence coding for MAGE-A1, placed after the Vacciniavirus H6 promoter, was cloned into the pKILGPT vector, creating donor plasmid MAW035. A similar MAGE-A4 donor plasmid vector was constructed by replacing the MAGE-A1 cDNA with the MAGE-A4 cDNA. The MAGE-A3 cDNA was digested with Pst1 and XbaI, blunt ended, the insert was gel purified and ligated into the SmaI site of the PsC11 vector. For the PsC11 vector, see Chakrabati et al. (1985) *Mol. Cell Biol.* 5: 34–3–3409.

The donor plasmids was transfected into CEF cells containing the genomic DNA of vaccinia strain WR, yielding recombinant vaccinia viruses WR-MAGE-A1, WR-MAGE-A4 and WR-MAGE-A3, respectively, by way of in vivo recombination and selected with BrdU and X-gal. The procedure can be found in, e.g., Perkins et al. (1989) *J. Virol.* 63: 3829–3936.

EXAMPLE 3

Generation of Recombinant Alvac-Mage-A1 Viruses

A MAGE-A1 coding sequence, placed after the Vaccinia Virus H6 promoter, was cloned into the pUC8-based vector to generate donor plasmid MAW036.

Recombinant ALVAC-MAGE-A1 virus was generated by using the donor plasmid MAW036 and following well known procedures, e.g., as described in *Current Protocols in Molecular Cloning* (Ausubel et al., John Wiley & Sons, New York) and Ferrari et al. (*Blood* 90: 2406–2416, 1997).

Recombinant canarypox virus ALVAC-MAGE-A3 split (also referred to herein as "ALVAC-MAGE-A3" for simplicity) expressed two truncated overlapping fragments of MAGE-A3, one fragment spanning amino acids 1–196 and the other fragment spanning amino acids 147–199. In the recombinant virus, each fragment was contained in a separate expression cassette, each under the control of the vaccinia virus H6 promoter, and both cassettes were inserted at the C3 site in the ALVAC genome.

The vCP1563 recombinant was generated as follows. The MAGE-A3 (1–196) DNA fragment was generated and linked to the vaccinia H6 promoter by standard PCR procedures with plasmid pTZ18R (containing full length MAGE-A3 cDNA) as template. The MAGE-A3 (147–199) DNA fragment was generated and linked to the H6 promoter in the same way. These two fragments were then subcloned into a plasmid such that the cassettes were flanked by ALVAC DNA from the C3 insertion site. The organization of these elements in the plasmid was as follows: ALVAC C3 left flanking arm, MAGE-A3 (147–299)/H6, MAGE-A3 (1–196)/H6, ALVAC C3 right flanking arm. This ALVAC C3 site donor plasmid containing the MAGE-A3 (1–196) and (147–299) fragment expression cassettes was designated pC3MAGE3 split.

The ALVAC-MAGE-A3 recombinant was generated by in vivo recombination between the pC3MAGE3 split donor plasmid and ALVAC genomic DNA following standard procedures. Recombinant virus was selected by hybridization with MAGE-3-specific DNA probes and plaque was purified. The resulting ALVAC-MAGE-A3 recombinant was given the laboratory designation vCP1563. Expression analysis with MAGE-3-specific antisera confirmed the expression of MAGE-A3 (1–196) and (147–299) polypeptides in cells infected with ALVAC-MAGE-A3 (vCP1563).

EXAMPLE 4

Generation of Recombinant Adenoviruses

For the construction of the recombinant adenovirus, the plasmid pAd-CMVIcpA-MAGE-A4 (containing the MAGE-A4 cDNA under the control of the CMV promoter) was obtained by inserting into the NotI site of vector pAd-CMVIcpA (provided by Celia GARCIA and Thierry RAGOT, URA CNRS 1301), the MAGE-A4 complete cDNA.

The recombinant adenovirus Ad-MAGE-A4 was generated by in vivo homologous recombination in cell line 293 between pAd-CMVIcpA-MAGE-A4 and βd-ggal genomic DNA. Briefly, 293 cells were cotransfected with 5 µg of plasmid pAd-CMVIcpA-MAGE-A4 linearized with XmnI and 5 µg of the large ClaI fragment of Adeno-βgal DNA (Stratford-Perricaudet et al. (1992), *J. Clin. Invest.*, 90: 626–630 and Patent FR 9603207. The recombinant adenovirus was plaque purified and the presence of the transgene was assessed by restriction analysis of the adenoviral DNA. Recombinant adenoviruses were propagated in 293 cells and purified by double cesium chloride density centrifugation. The viral stocks were stored in aliquots with 10% glycerol in liquid nitrogen and titered by plaque assay using 293 cells.

Recombinant adenovirus Ad-MAGE-A3 was generated according to essentially the same procedure described above, but MAGE-A3 cDNA was derived from a λgt10 recombinant clone.

EXAMPLE 5

Recombinant Retrovirus and Infection of Cell Lines

The M1-CSM retroviral vector encodes the full length MAGE-A1 protein, under the control of the LTR, and the truncated form of the human low affinity nerve growth factor receptor (ΔLNGFr) driven by the SV40 promoter (Mavilio F. et al., *Blood* 83: 1988–1997, 1994). EBV-B cells or PHA-activated T cells were transduced by coculture with irradiated packaging cell lines producing the M1-CSM vector in the presence of polybrene (8 μg/ml). After 72 hours, lymphocytes were harvested and seeded in fresh medium. The percentage of infected cells was evaluated 48 hours later by flow cytomemtry for LNGFr expression with the mAb 20.4 (ATCC, Manassas, Va., USA). The LNGFr positive cells were purified by magnetic cell sorting using Rat anti-mouse IgG1-coated beads (Dynabeads M-450, DYNAL A. S. N012 Oslo, Norway).

EXAMPLE 6

Materials and Methods

Cell lines and Media

The Epstein Barr Virus (EBV) immortalized B cells (hereafter referred as to EBV-B cells) were obtained following the standard protocol. EBV-B cells and the melanoma cell lines were cultured in Iscove's modified Dulbecco medium (IMDM) (GIBCO BRL, Gaitherburg, Md., USA) supplemented with 10% fetal calf serum (FCS) (GIBCO BRL), 0.24 mM L-asparagine, 0.55 mM L-arginine, 1.5 mM L-glutamine (AAG), 100 U/ml penicillin and 100 μg/ml streptomycin. Hela and COS-7 cells were maintained in H16 medium (GIBCO BRL) supplemented with 10% FCS.

Cytokines

Human recombinant IL-2 was purchased from CHIRON BV (Amsterdam, Netherlands) or EUROCETUS (Amsterdam, Netherlands), or provided by BIOGEN (Geneva, Switzerland). Human recombinant IL-7 was purchased from GENZYME (Cambridge, Mass.). Human recombinant GM-CSF was purchased from SANDOZ (Leucomax, Sandoz Pharma, Basel, Switzerland) or SCHERING PLOUGH (Brinny, Ireland). Human recombinant IL-4, IL-6 and IL-12 were produced by the present inventors.

Processing of Human Blood

Peripheral blood was obtained from the local blood bank (non cancer patients, namely, hemochromatosis patients) as standard buffy coat preparations. Peripheral blood mononuclear cells (PBMC) were isolated by centrifugation on Lymphoprep (NYCOMED PHARMA, Oslo, Norway). In order to minimize contamination of PBMC by platelets, the preparation was first centrifuged for 20 min at 1000 rpm at room temperature. After removal of the top 20–25 ml containing most of the platelets, the tubes were centrifuged for 20 min at 1500 rpm at room temperature. PBMC were depleted of T cells by rosetting with sheep erythrocytes (BIO MÉRIEUX, Marcy-l'Etoile, France) treated with 2-aminoethyl-isothiouronium (SIGMA, St. Louis, Mo., USA). Rosetted T cells were treated with NH$_4$Cl (160 mm) to lyse the sheep erythrocytes and washed. The CD8$^+$ T lymphocytes were isolated by positive selection using an anti-CD8 monoclonal antibody coupled to magnetic microbeads (MILTENYI BIOTECH, Germany) and by sorting through a magnet. The CD8$^+$ T lymphocytes were frozen, and thawed the day before the start of the primary culture and cultured overnight in Iscove's medium containing L-asparagine (0.24 mM), L-arginine (0.55 mM), L-glutamine (1.5 mm), 10% human serum (hereafter referred to as complete Iscove's medium) and supplemented with 2.5 U/ml IL-2.

The lymphocyte-depleted PBMC were frozen or used immediately for dendritic cell cultures. Cells were left to adhere for 1–2 hrs at 37° C. in culture flasks (Falcon, BECTON DICKINSON LABWARE, Franklin Lakes, USA) at a density of 2×10$^6$ cells/ml in RPMI 1640 medium (GIBCO BRL) supplemented with L-asparagine (0.24 MM), L-arginine (0.55 mM), L-glutamine (1.5 mM) and 10% fetal calf serum (hereinafter referred to as complete RPMI medium). Non-adherent cells were discarded and adherent cells were cultured in the presence of IL-4 (100 U/ml) and GM-CSF (100 ng/ml) in complete RPMI medium. For experiments in Examples 7 and 8, cultures were fed on day 2 and day 4 by removing ⅓ of the volume of the medium and adding fresh medium with IL-4 (100 U/ml) and GM-CSF (100 ng/ml); and on day 6 or 7, the non-adherent cell population was used as a source of enriched dendritic cells. For experiments in Example 9, cultures were fed on day 2 by removing ⅓ of the volume of the medium and adding fresh medium with IL-4 (100 U/ml) and GM-CSF (100 ng/ml) and were frozen on day 4; and on the day before each stimulation, dendritic cells were thawed and grown overnight in complete medium supplemented with 100 U/ml IL-4 and 100 ng/ml GM-CSF. For experiments in Examples 10–11, cultures were fed on day 2 and 4 by removing ½ or ⅓ of the volume of the medium and adding fresh medium with IL-4 (100 U/ml) and GM-CSF (100 ng/ml); and on day 5 or day 7, the non-adherent cell population was used as a source of enriched dendritic cells.

Interferon γ Production Assay 5000 target cells were cultured overnight with 2000 CTL in 100 μl per well complete Iscove's medium supplemented with 25 U/ml IL-2 in 96 well round bottom plates. The production of interferon γ (IFN-γ) was measured in 50 μl supernatant by ELISA (Biosource).

cDNAs Encoding HLA-class I Molecules

The HLA-A*0201 coding sequence was obtained from a cDNA library of cell line BB49, cloned into expression vector pcDNAI/Amp (INVITROGEN). The HLA-A3 coding sequence was isolated from a cDNA library of cell line LB33 cloned into expression vector pcDNA3 (INVITROGEN). The HLA-B*4402 coding sequence was isolated by RT-PCR from cell line LB33 and cloned in expression vector pcDNAI/Amp. The HLA-B*40012 (B60) coding sequence was derived by RT-PCR from cell line HA7-RCC and cloned in expression vector pcDNA3. The HLA-Cw3 coding sequence was cloned in expression vector pCR3. The HLA-Cw5 was isolated from cell line LB373 by RT-PCR and cloned into pcDNA3. The HLA-B*0801, B*4002 (B61), Cw*02022, and Cw*0701 coding sequences were amplified by RT-PCR using RNA of LB 1118-EBV-B cells as the template. The HLA-B*5301 coding sequence was amplified by RT-PCR using RNA of EBV-B cells of patient LB 1118 as the template. The HLA-B7 and HLA-B40 segments were isolated as described in Examples 12 and 13. PCR products were cloned into expression vector pcDNA3. DNA was extracted from recombinant clones and sequenced partially on the sense and partially on the antisense strand by the dideoxy-chain termination method (Thermosequenase™ cycle sequencing kit, Amersham).

Peptides Recognition Assay

Peptides were synthesized on solid phase using F-moc for transient NH2-terminal protection and were characterized using mass spectrometry. All peptides were >80% pure, as indicated by analytical HPLC. Lyophilized peptides were dissolved in DMSO and stored at −20° C. Target cells were labeled with Na($^{51}$Cr)O$_4$, washed, and incubated for 15 min in the presence of peptide. CTL clone was then added at an effector-to-target ratio of 5:1 to 10:1. Chromium release was measured after incubation at 37° C. for 4 hours.

EXAMPLE 7

A Mage-A1 Derived Peptide Presented by HLA-Cw3 Molecules to Cytolytic T Lymphocytes Isolation of MAGE-A1 Specific CTL Clone LB1137 462/F3.2

Autologous dendritic cells from donor LB 1137 (HLA-A2 A3 B4402 B60 Cw3 Cw5) were infected with the ALVAC-MAGE-A1 at a multiplicity of infection of 30 in RPMI containing 10% FCS at 37° C. under 5% CO$_2$. After 2 hours, the infected dendritic cells were washed. For in vitro stimulation, 150,000 CD8$^+$ T lymphocytes and 30,000 infected dendritic cells were cocultured in microwells in 200 μl Iscove's medium containing L-asparagine (0.24 mM), L-arginine (0.55 mM), L-glutamine (1.5 mM), 10% human serum (hereafter referred to as complete Iscove's medium) and supplemented with IL-6 (1000 U/ml) and IL-12 (10 ng/ml). The CD8$^+$ lymphocytes were weekly restimulated with autologous dendritic cells freshly infected with the ALVAC-MAGE-A1 and grown in complete Iscove's medium supplemented with IL-2 (10 U/ml) and IL-7 (5 ng/ml).

After several rounds of stimulation; an aliquot of each microculture was tested for specific lysis of autologous target cells. Autologous EBV-B cells were infected for two hours with either the parental vaccinia WR (batch LVAR) or the WR-MAGE-A1 construct (vP 1267), using a multiplicity of infection of 20, and labeled with Na($^{51}$Cr)O$_4$. Afterwards, EBV-B cells (target cells) were washed, and added to the responder cells at an effector to target ratio of approximately 40:1. Unlabeled K562 cells were also added (5×10$^4$ per V-bottomed microwell) to block natural killer activity. Chromium release was measured after incubation at 37° C. for 4 hours. The individual microcultures were tested in duplicate on each target.

The positive microcultures were cloned by limiting dilution, using autologous EBV-B cells infected with recombinant Yersinia expressing the YopE$_{130}$-MAGE-A1 protein as stimulating cells, and allogeneic EBV-B cells (LG2-EBV) as feeder cells. The cultures were restimulated similarly on day 7, and clones were maintained in culture by weekly restimulation with allogeneic EBV-B cells (LG2-EBV) in complete Iscove's medium supplemented with 0.5 Mg/ml PHA-HA16 (Murex) and 50 U/ml of IL-2. At day 3 after restimulation, the clones were washed to remove the PHA-HA16 in the culture medium. The clones were tested for specific lysis of autologous EBV-B cells infected with the vaccinia-MAGE-A1 construct. Clone LB1137 462/F3.2 was found positive (FIG. 3a) and used in subsequent experiments.

The MAGE-A1 Epitope is Presented to CTL by RHA-Cw3 Molecules

As donor LB 1137 expresses a number of different HLA molecules as described supra, each HLA was tested to determine which one presented the antigen recognized by CTL LB1137 462/F3.2.

COS cells were transfected with plasmids encoding one of the six HLA-class I molecules together with the cDNA of MAGE-A1. In brief, 1.5×10$^4$ COS cells distributed in microwells were cotransfected with 50 ng of plasmid pcD-NAI containing the MAGE-A1 cDNA and 50 ng of plasmid pcDNA3 containing the cDNA coding for one of the six HLA-class I molecules that were expressed by donor LB1137, using 1 μl of Lipofectamine reagent (Gibco BRL). The COS cells were incubated 5 hours at 37° C. and 8% CO$_2$ in the transfection mixture and 200 μl of culture medium was added. After overnight culture, transfectants were tested for their ability to stimulate the production of IFN-γ by clone LB1137 462/F3.2. Briefly, 1500 CTLs were added to each microwell containing transfected cells, in a final volume of 100 μl of Iscove's complete medium containing 25 U/ml of IL-2. After 24 hours, 50 μl supernatant was tested for its IFN-γ content in a WEHI bioassay which measured the cytotoxic effect of IFN-γ on cells of WEHI-164 clone 13 in a MTT calorimetric assay. Only those cells transfected with both HLA-Cw3 and MAGE-A1 stimulated CTL clone LB1137 462/F3.2 to produce IFN-γ (FIG. 3b). COS cells transfected with MAGE-A1 or HLA-Bw3 alone did not stimulate the CTL clone.

Antigenic Peptides and CTL Assay

In order to identify the MAGE-A1 peptide recognized by clone LB1137 462/F3.2, peptides (16 amino-acids) corresponding to parts of the MAGE-A1 protein were synthesized, loaded on the autologous EBV-B cells and tested for recognition. Peptides were synthesized on solid phase using F-moc for transient NH$_2$-terminal protection. Lyophilized peptides were dissolved at 20 mg/ml in DMSO, diluted at 2 mg/ml in 10 mM acetic acid and stored at −20° C.

Peptides were tested in chromium release assays in which 1000 $^{51}$C-labeled target cells were incubated with 10 μg/ml of peptide in 96-well microplates (100 μl/well) for 20 min at room temperature, prior to adding 100 μl medium containing 10,000 CTL. The assay was terminated after 4 hours of incubation at 37° C. and 8% CO2.

Autologous EBV-B cells incubated with peptide DGREHSAYGEPRKLLT (MAGE-A1$_{225-240}$) (SEQ ID NO: 37) were recognized by CTL LB1137 462/F3.2 (FIG. 3c). This long peptide contained a 9-amino-acid peptide SAYGEPRKL (MAGE-A1$_{230-238}$) (SEQ ID NO: 2) which contained adequate anchor residues for HLA-cw3: a Y in position 3 and a L at the c-terminus. DGREHSAYGEPRKLLT (SEQ ID NO: 37) was screened for prediction of an HLA-Cw3 binding peptide with the software available at the website of the National Institute of Health. Peptide SAYGEPRKL (MAGE-A1$_{230-238}$) (SEQ ID NO: 2) had the highest score for binding to HLA-Cw3. It was recognized by CTLLB1137 462/F3.2 in a cytotoxicity assay at an effector to target ratio of 10:1 (FIG. 3C).

Recognition by CTL Clone LB1137 462/F3.2 of HLA-Cw3 Positive Tumor Cells Expressing MAGE-A1

The activation of CTL LB1137 462/F3.2 by tumor cell lines that express HLA-Cw3 and MAGE-A1 was tested in an IFN-γ production assay. CTL clone LB1137 462/F3.2 recognized the HLA-Cw3 positive tumor cell line LB17-MEL which expresses MAGE-A1 (FIG. 3d). The melanoma cell line Mi 665/2 E+ clone 2, that was transfected with a genomic fragment containing the open reading frame of MAGE-A1 (as described in U.S. Pat. No. 5,342,774), was also recognized by clone LB1137 462/F3.2, whereas the parental cell line Mi 665/2 was not recognized.

EXAMPLE 8

A Mage-A1 Derived Peptide Presented by HLA-B5301 Molecules to Cytolytic T Lymphocytes Isolation of MAGE-A1 Specific CTL Clone LB1801 456/H7.11

Autologous dendritic cells from donor LB1801 (HLA-A201, A28, B4401, B5301, Cw04, Cw0501) were infected with the ALVAC-MAGE-A1 construct at a multiplicity of infection of 30 in RPMI containing 10% FCS at 37° C. under 5% $CO_2$. After 2 hours, the infected dendritic cells were washed twice. For in vitro stimulation, 150,000 CD8+ lymphocytes and 30,000 infected dendritic cells were cocultured in round bottomed microwells in 200 microliters Iscove's medium containing L-asparagine (0.24 mM), L-arginine (0.55 mM), L-glutamine (1.5 mM), 10% human serum (hereafter referred as complete Iscove's medium) and supplemented with IL-6 (1000 U/ml) and IL12 (10 ng/ml). The CD8+ lymphocytes were weekly restimulated with autologous dendritic cells freshly infected with the ALVAC-MAGE-A1 construct and grown in complete Iscove's medium supplemented with IL-2 (10 U/ml) and IL-7 (5 ng/ml).

Autologous EBV-B cells were, infected for 2 hours with either the parental vaccinia WR (vP1170) or the recombinant vaccinia WR-MAGE-A1 (vP1188) using a multiplicity of infection of 20, and labeled with $Na(^{51}Cr)O_4$. Target cells were washed, and added to the responder cells at an effector to target ratio of approximately 40:1. Unlabeled K562 were also added ($5 \times 10^4$ per V-bottomed microwell) to block natural killer activity. Chromium release was measured after incubation at 37° C. for 4 hours. The individual microcultures were tested in duplicate on each target.

The microcultures containing cells that specifically lysed autologous EBV-B cells infected with the vaccinia-MAGE-A1 construct were cloned by limiting dilution using autologous EBV-B cells previously infected with the Yersinia expressing $YopE_{1-130}$-MAGE-A1 as stimulating cells, and allogeneic EBV-B cells (LG2-EBV) as feeder cells. CTL clones were maintained in culture by weekly restimulation in complete Iscove's medium supplemented with 50 U/ml of IL2. The clones were tested for specific lysis of autologous EBV-B cells infected with the vaccinia-MAGE-A1 construct. Clone LB1801 456/H7.11 was found positive (FIG. 4a) and used in the following experiments. The CTL was restimulated weekly with LG2-EBV as feeder cells and alternately, purified phytohaemagglutin (PHA-HA16; MUREX) (0.5 mg/ml) or autologous EBV-B cells previously infected with the Yersinia-$YopE_{1-130}$-MAGE-A1.

Antigenic Peptides and CTL Assay

In order to identify the MAGE-A1 peptide recognized by clone LB1801 456/H7.11, peptides (16 amino-acids) corresponding to parts of the MAGE-A1 protein were synthesized, loaded on the autologous EBV-B cells and tested for recognition. Peptides were synthesized on solid phase using F-moc for transient NH2-terminal protection. Lyophilized peptides were dissolved at 20 mg/ml in DMSO, diluted at 2 mg/ml in 10 mM acetic acid and stored at −20° C. Peptides were tested in chromium release assay where 1000 $^{51}$Cr-labeled target cells were incubated for 15 min at room temperature in V-bottomed microplates with 5 µg/ml of peptide, before adding an equal volume containing 5,000 CTLs. The assay was terminated after 4 hours of incubation at 37° C. and 8% CO2. Peptides QVPDSDPARYEFLWGP (MAGE-A1 253–268) (SEQ ID NO: 38) and SDPARYEFLWGPRALA (MAGE-A1 257–272) (SEQ ID NO: 39) scored positive.

Identification of the HLA Presenting Molecule

To know which HLA molecule presented both 16-mers peptides to CTL clone LB1801 456/H7.11, peptides were tested in a chromium release assay using, as target cells, EBV-B cells from different donors that shared HLA molecules with donor LB1801. Clone LB1801 456/H7.11 were able to recognize the peptide only when presented by autologous cells (Table 4). Because, no EBV-B cells expressing the HLA-B5301 molecule was tested, the cDNA coding for HLA-B5301 of donor LB1801 was isolated.

The HLA-B5301 coding sequence was amplified by RT-PCR using RNA of LB1801-EBV-transformed B cells as template. The PCR products were cloned into expression vector pcDNA3 (Invitrogen BV, the Netherlands). DNA was extracted from recombinant clones and sequenced partially on the sense and partially on the antisense strand to check that it was a sequence encoding HLA-B5301. The sequence for HLA-B5301 is described by Mason and Pasham (1998), *Tissue Antigens* 51: 417–466.

COS-7 cells were transfected with plasmids encoding HLA-B5301 molecule together with MAGE-A1 cDNA. In brief, $1.5 \times 10^4$ COS-7 cells distributed in microwells were cotransfected with 100 ng of plasmid pcDNAI containing the MAGE-A1 cDNA, 100 ng of plasmid pcDNA3 containing the cDNA coding for HLA-B5301 molecule of donor LB 1801, and one microliter of lipofectamine (Gibco BRL). The COS-7 cells were incubated 24 hours at 37° C. and 8% $CO_2$. These transfectants were then tested for their ability to stimulate the production of TNF by clone LB1801 456/H7.11. Briefly, 1,500 CTLs were added to the microwells containing

TABLE 4

| Target Cells | HLA Typing | | | | No Peptide | SDPARYEF-LWGPRALA |
|---|---|---|---|---|---|---|
| | | | | | \% of Lysis | |
| LB1801 | A2 A28 | B4402 B53 | CwD4 Cw0501 | | 5 | 41 |
| LB1118 | A2 A3 | B8 B61 | Cw2 Cw7 | | 19 | 15 |
| LB33 | A24 A28 | B13 B4402 | Cw6 Cw7 | | 22 | 18 |
| LB1158 | A2 A3 | B35 B51 | Cw1 Cw4 | | 6 | 4 |
| LB1137 | A2 A3 | B4402 B60 | Cw3 Cw5 | | 5 | 3 |
| LG2 | A24 A32 | B3503 B4403 | Cw4 | | 1 | 4 |
| LB1819 | A2 | B44 B57 | Cw5 Cw7 | | 0 | 4 |
| LB1161 | A3 A26 | B39 B4402 | | | 1 | 8 |
| LB1213 | A24 | B18 B35 | Cw4 Cw7 | | 0 | 4 |

Table 4: Lysis by CTL LB1801 456/H7.11 of various EBV-B cells (target cells) pulsed with MAGE-A1 peptide.

EBV-B cells were 51Cr labeled and incubated with CTL at an effector to target cell ratio of 5/1 in the presence (or not) of 5 microgrammes of peptide SDPARYEFLWGPRALA (SEQ ID NO: 39). Chrominum release was measured after 4 hours.

the transfectants, in a total volume of 100 ml of Iscove's complete medium containing 25 U/ml of IL-2. After 24 hours, the supernatant was collected and its TNF content was determined by testing its cytotoxic effect on cells of WEHI-164 clone 13 in a standard MTT colorimetric assay. The cells transfected with both HLA-B53 and MAGE-A1 stimulated CTL clone LB1801 456/H7.11 to produce TNF (FIG. 4b). COS-7 cells transfected with MAGE-A1 or HLA-B53 alone did not stimulate the CTL clone.

Identification of the Antigenic Peptide

To identify the sequence of the shortest synthetic peptide recognized by clone LB1801 456/H7.11, we compared the lysis by the CTL of autologous EBV-B cells, loaded with the MAGE-AL peptide SDPARYEFLWGPRALA (MAGE-A1 257–272) (SEQ ID NO: 39) or the MAGE-A4 peptide GSNPARYEFLWGPRAL (MAGE-A4 264–279) (SEQ ID NO: 40), in a chromium release at an effector target ratio of 10 and a final concentration of peptide of 5 µg/ml. The MAGE-A1 peptide, but not the MAGE-A4 peptide, was recognized. The 10-mer peptide SDPARYEFLW (SEQ ID NO: 41) and the 9-mer peptide DPARYEFLW (SEQ ID NO: 42) were then synthesized and tested in a cytotoxic assay at an effector to target ratio of 5. Both peptides were recognized. The shorter peptide was then tested at different concentration at an effector to target ratio of 10 (FIG. 4c). Half-maximal lysis was obtained at between 10 and 100 ng/ml.

EXAMPLE 9

A Mage-A4 Derived Peptide Presented by HLA-A2 Molecules to Cytolitic T Lymphocytes Isolation of 4AGE-A4 Specific CTL Clone LB1137 H4.13

Autologous dendritic cells from donor LB 1137 (HLA-A2, -A3, -B4402, -B60, -Cw3, -Cw5) were infected with the Ad-MAGE-A4 construct at a multiplicity of infection of 200 in RPMI containing 10% FCS at 37° C. under 5% $CO_2$. After 2 hours, the infected dendritic cells were washed. For in vitro stimulation, 150,000 $CD8^+$ T lymphocytes and 30,000 infected dendritic cells were cocultured in microwells in 200 µl Iscove's medium containing L-asparagine (0.24 mM), L-arginine (0.55 mM), L-glutamine (1.5 mM), 10% human serum (hereafter referred to as complete Iscove's medium) and supplemented with IL-6 (1000 U/ml) and IL-12 (10 ng/ml). The $CD8^+$ lymphocytes were weekly restimulated with autologous dendritic cells freshly infected with the Ad-MAGE-A4 construct and grown in complete Iscove's medium supplemented with IL-2 (10 U/ml) and IL-7 (5 ng/ml) These cells were tested as responder cells in the following assay.

Autologous EBV-B cells were infected for 2 hours with either the parental vaccinia WR parent (batch vP1171 or batch L VAR) or the recombinant vaccinia WR-MAGE-A4 (batch vP1545) using a multiplicity of infection of 20, and labeled with $Na(^{51}Cr)O_4$. These target cells were washed, and added to the responder cells at an effector to target ratio of approximately 40:1. Unlabeled K562 cells were also added ($5 \times 10^4$ per V-bottomed microwell) to block natural killer activity. Chromium release was measured after incubation at 37° C. for 4 hours. The individual microcultures were tested in duplicate on each target.

The microcultures containing cells that specifically lysed autologous EBV-B cells infected with the vaccinia-MAGE-A4 construct were cloned by limiting dilution using, as stimulating cells, autologous EBV-B cells infected with the recombinant Yersinia expressing $YopE_{1-130}$-MAGE-A4 (described above), and using allogeneic EBV-B cells (LG2-EBV) as feeder cells. Infection of EBV-B cells with Yersinia $YopE_{1-130}$-MAGE-A4 was done as follows: one colony of Yersinia MRS40 (pABL403) containing pMS621-MAGE-A4 ($YopE_{1-130}$-MAGE-A4) was grown overnight at 28° C. in LB medium supplemented with nalidixic acid, sodium m-arsenite and chloramphenicol. From this culture, a fresh culture at an OD (600 nm) of 0.2 was then amplified at 28° C. for approximately 2 hours. The bacteria were then washed in 0.9% NaCl and resuspended at $10^8$ bacteria per ml in 0.9% NaCl. Irradiated EBV-B cells were infected at a multiplicity of infection of 20 in complete RPMI 1640 (culture media was supplemented with 10% FCS, and with L-arginine (116 mg/ml), L-asparagine (36 mg/ml), L-glutamine (216 mg/ml). Two hours after infection, gentamycin (30 µg/ml) was added for the next two hours, and the cells were finally washed 3 times. CTL clones were maintained in culture by weekly restimulation with either Yersinia $YopE_{1-130}$-MAGE-A4 infected EBV-B cells, HLA-A2 melanoma cell line QUAR (LB1751-MEL) that expressed MAGE-A4, or PHA (0.5 µg/ml) in complete Iscove's medium supplemented with 50 U/ml of IL-2. The clones were tested for specific lysis of autologous EBV-B cells infected with the vaccinia-MAGE-A4 construct. Clone LB1137 H4.13 was found positive (FIG. 5a) and used in the following experiments.

The MAGE-A4 Epitope is Presented to CTL by HLA-A2 Molecules

The lysis by CTL clone LB1137 H4.13 of EBV-B cells infected with the vaccinia-MAGE-A4 construct was inhibited by addition of an anti-HLA-A2 monoclonal antibody but not by addition of an anti-HLA-A3 or an anti-HLA-B,C monoclonal antibody. This indicated that the MAGE-A4 epitope was presented by HLA-A2 molecules.

COS cells were transfected with plasmids encoding the HLA-A2 molecule together with the cDNA of MAGE-A4. In brief, $1.5 \times 10^4$ COS cells distributed in microwells were cotransfected with 50 ng of plasmid pcDNAI containing the MAGE-A4 cDNA, 50 ng of plasmid pcDNA1/Amp containing the genomic DNA coding for the HLA-A2 molecule and 1 µl of DMRIEC (Gibco BRL). The COS cells were incubated 24 hours at 37° C. and 8% $CO_2$. These transfectants were then tested for their ability to stimulate the production of TNF by clone LB1137 H4.13. Briefly, 2000 CTL were added to the microwells containing the transfectants, in a total volume of 100 µl of Iscove's complete medium containing 25 U/ml of IL-2. After 24 hours, the supernatant was collected and its TNF content was determined by testing its cytotoxic effect on cells of WEHI-164 clone 13 in a standard MTT colorimetric assay. The cell transfected with both HLA-A2 and MAGE-A4 stimulated CTL clone LB1137 H4.13 to produce TNF (FIG. 5b). COS cells transfected with MAGE-A4 or HLA-A2 alone did not stimulate the CTL clone.

Determination of the Antigenic Peptide

In order to identify the MAGE-A4 peptide recognized by clone LB1137 H4.13, PCR reactions were performed using the MAGE-A4 cDNA as template, an upstream primer (S) consisting of the first nucleotides of the open reading frame of MAGE-A4 and 8 downstream primers (AS1 to AS8) (FIG. 6), separated from each other by approximately 100–120 bp in the open reading frame of MAGE-A4. The PCR was performed for 30 cycles (1 min at 94° C., 2 min at 63° C. and 3 min at 72° C. This led to the amplification of 8 fragments of MAGE-A4 of different lengths (MAGE-A4 (1) to MAGE-A4(8)), the longer one (MAGE-A4(1)) containing the entire open reading frame of MAGE-A4. PCR products were ligated into the pcDNA3.1/V5/His-TOPO vector and the recombinant vectors were transformed into E. coli cells (Topo TA cloning kit, Invitrogen). Colonies were analyzed by PCR and DNA of positive clones. was extracted and used to transfect HeLa cells together with a plasmid encoding the HLA-A2 molecule. Briefly, $2 \times 10^4$ HeLa cells distributed in microwells were cotransfected with 50 ng of plasmid pcDNA3.1/V5/His-TOPO containing the MAGE-4A fragment, 50 ng of plasmid pcDNA1/Amp containing the genomic DNA coding for the HLA-A2 molecule and 1 µl of Lipofectamine (Gibco BRL). The HeLa cells were incubated 24 hours at 37° C. and 8% $CO_2$. These transfectants were then tested for their ability to stimulate the production of TNF by clone LB1137 H4.13 as described above. Transfection with inserts S-AS1 and S-AS2 were positite, transfections with the other constructs were negative. This led to the identification of a MAGE-4A fragment of 130 bp, TGATGGGAGGGAGCACACTGTCTATGGG-GAGCCCAGGAAACTGCTCACCCAAGATTG GGTG-CAGGAAAACTACCTGGAGTACCGGCAGG-TACCCGGCAGTAATCCTGCGCGCTA TGAGTTCCTGTGGGGT (SEQ ID NO: 43), encoding the epitope recognized by clone LB1137 H4.13.

The sequence of the putative fragment of the MAGE-A4 protein encoded by this region was screened for prediction of an HLA-a2 binding peptide with the software available at the website of the National Institute of Health. Peptide GVYDGREHTV (SEQ ID NO: 44) (MAGE-A4$_{230\text{-}239}$) had the highest score. It was synthesized and tested in a cytotoxicity assay at an effector to target ratio of 10:1. Peptide GVYDGREHTV (MAGE-A4$_{230\text{-}239}$) (SEQ ID NO: 44) was found to sensitize autologous target cells to lysis by clone LB1137 H4.13 (FIG. 5C).

Recognition by CTL Clone LB1137 H4.13 of HLA-A2 Cells Expressing MAGE-A4

As indicated in FIG. 5d, CTL clone LB1137 H4.13 was able to lyse HLA-A2 melanoma cell line QUAR (LB1751-MEL) that expressed MAGE-A4.

EXAMPLE 10

A Mage-A1 Peptide Presented by KLA-Cw2 to CTL Clone LB1118 466/D3.31

Isolation of CTL Clone LB1118 466/D3.31

Dendritic cells ($3\times10^6$/ml) from donor LB 1118 (HLA-A*0201, A3, B*0801, B*4002, Cw*02022, Cw*0701) were infected with the ALVAC-MAGE-A1 at a multiplicity of infection of 30 in RPMI supplemented with AAG and 10% FCS at 37° C. under 5% $CO_2$. After 2 hours, the infected dendritic cells were washed. 150,000 autologous CD8$^+$ T lymphocytes and 30,000 infected dendritic cells were cocultured in microwells in 200 $\mu$l complete Iscove's medium and supplemented with IL-6 (1000 U/ml) and IL-12 (10 ng/ml). The CD8$^+$ lymphocytes were restimulated on days 7 and 14 with autologous dendritic cells freshly infected with the ALVAC-MAGE-AL and grown in complete Iscove's medium supplemented with IL-2 (10 U/ml) and IL-7 (5 ng/ml).

The microcultures containing proliferating CD8+ T cells were assessed on day 21 for their capacity to lyse autologous EBV-B cells infected with vaccinia-MAGE-A1 (vP 1188). EBV-B cells infected with parental vaccinia (vP1170) were used as a negative control. Infected EBV-B cells (target cells) were washed and added to the responder cells at an effector to target ratio of approximately 40:1. Unlabeled K562 cells were also added ($5\times10^4$ per V-bottomed microwell) to block natural killer activity. Chromium release was measured after incubation at 37° C. for 4 hours. The individual microcultures were tested in duplicate on each target. In a first experiment, an anti-MAGE-A1 reactivity was detected in 3 microcultures out of 96. 13% of the microcultures contained responder cells that lysed targets infected with either vaccinia or vaccinia-MAGE-A1, but not the uninfected targets. This result indicated that the ALVAC and vaccinia vectors shared antigens recognized by CTL. In a second experiment, 2 microcultures scored positive in their anti-MAGE-A1 reactivity.

The positive microcultures (i.e., those that recognize autologous EBV-B cells infected with vaccinia-MAGE-A1 construct) were cloned by limiting dilution using, as stimulating cells, either autologous PHA-activated T cells transduced with a retrovirus encoding MAGE-A1, or autologous EBV-B cells transduced with the same retrovirus ($5\times10^3$ to $10^4$ cells per well in a 96-well plate). Allogeneic EBV-B cells ($5\times10^3$ to $10^4$ LG2-EBV-B cells per well in a 96-well plate) were used as feeder cells. CTL clones were tested for specific lysis of autologous EBV-B cells infected with the vaccinia-MAGE-A1 construct. The established CTL clones were maintained in complete IMDM supplemented with IL-2 (50 U/ml) and 0.5 $\mu$g/ml purified PHA (instead of stimulator cells) and passaged by weekly restimulation with allogeneic EBV-B cells ($1.5\times10^6$ LG2-EBV-B cells per well in a 24-well plate).

Figure 7A:
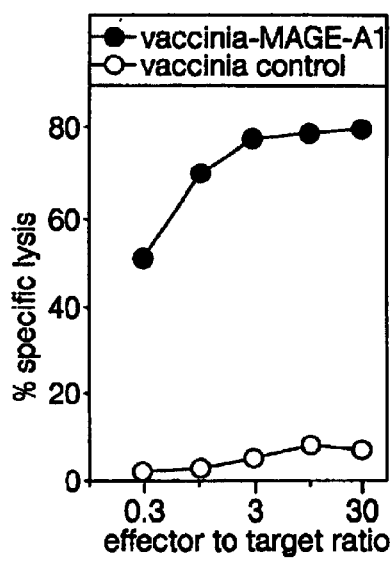
FIGS. 7A–D depict a MAGE-A1 peptide presented by HLA-Cw2 to CTL clone LB1118 466/D3.31.

Clone LB1118 466/D3.31 was identified as a positive clone that recognized autologous EBV-B cells infected with vaccinia-MAGE-A1 (FIG. 7A), or EBV-B transduced with a retrovirus encoding MAGE-A1.

Identification of the Peptide and the Presenting Molecule

Figure 7B:
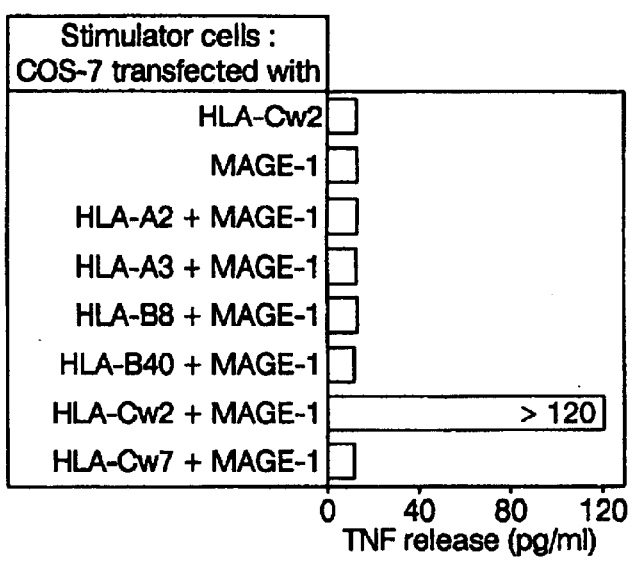
Figure 7C:
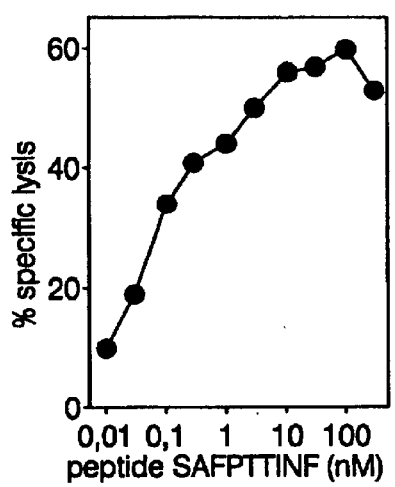
Figure 7D:
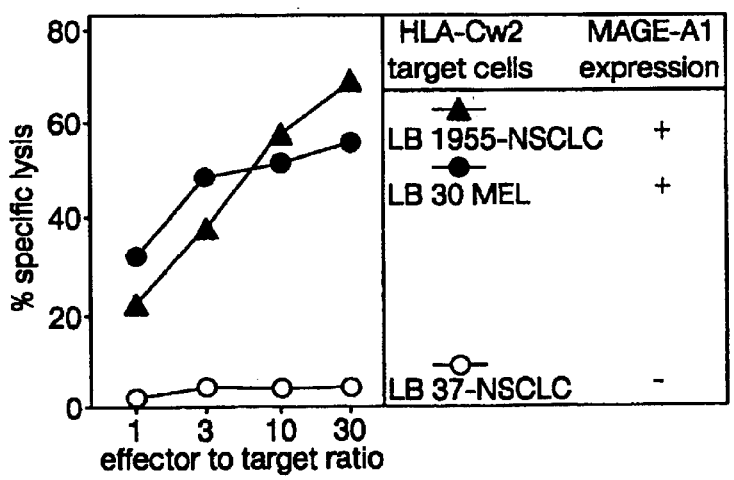

To identify the HLA molecule that presents the MAGE-A1 peptide by CTL clone LB1118 466/D3.31, COS cells were transfected with the MAGE-A1 cDNA, together with cDNAs coding for one of the putative HLA presenting molecules. These transfected cells were then tested for their ability to stimulate the CTL clone to produce TNF. CTL clone LB1118 466/D3.31 produced TNF upon stimulation by COS cells transfected with MAGE-A1 and HLA-Cw2 (FIG. 7B). To identify the MAGE-A1 peptide recognized by this CTL clone, a set of MAGE-A1 peptides of 12 amino acids that overlapped by 8 amino acids were screened. Autologous EBV-B cells were incubated with each of these peptides at a concentration of 1 $\mu$m, and tested for recognition by the CTL in a chromium release assay. Peptide ASAFPTTINFTR (MAGE-A1$_{61\text{-}72}$)(SEQ ID NO: 45) scored positive whereas the 16 amino-acid peptide SPQ-GASAFPTTINFTR (MAGE-A1$_{57\text{-}72}$), (SEQ ID NO: 46) scored negative. As information was not available for the residues anchoring a peptide in an HLA-Cw2 molecules, a number of shorter peptides were tested. Peptide SAFPT-TINF (MAGE-A1$_{62\text{-}70}$) (SEQ ID NO: 47) was subsequently found to be the shortest peptide capable of efficiently sensitizing autologous target cells to lysis by CTL clone LB1118 466/D3.31, with a half-maximal lysis obtained at ~0.1 nM (FIG. 7C). The natural processing of the antigen was shown by the lysis by CTL clone LB1118 466/D3.31 of HLA-Cw2 tumor cell lines that express MAGE-A1 (FIG. 7D).

EXAMPLE 11

A Mage-A1 Peptide Presented by HLA-A28 TO CTL Clone LB1801 456/H8.33

Dendritic cells were derived from donor LB 1801 (HLA-A*0201, A28, B*4401, B*5301, Cw4, Cw*0501). CTL clone LB1801 456/H8.33 was isolated by following essentially the same procedure as described in Example 10.

Briefly, immature dendritic cells derived from blood monocytes were infected with ALVAC-MAGE-A1 and used to stimulate autologous CD8+T cells in the presence of IL-6 and IL-12. Responder cells were restimulated once a week with autologous dendritic cells, infected with ALVAC-MAGE-A1, in the presence of IL-2 and IL-7. Responder cells were tested on day 28 for their lytic activity on autologous EBV-transformed B (EBV-B) cells infected with a vaccinia virus encoding MAGE-A1 (vaccinia-MAGE-A1).

Positive microcultures were subject to limiting dilution using EBV-B cells infected with Yersinia-MAGE-A1 as stimulating cells. CTL clone LB1801 456/H8.33 lysed autologous EBV-B cells infected with vaccinia-MAGE-A1

(FIG. 8A). CTL clone LB1801 456/H8.33 produced TNF upon stimulation by COS-7 cells transfected with HLA-A28 and MAGE-A1 (FIG. 8B). Peptide EVYDGREHSA (MAGE-A1$_{222-231}$) (SEQ ID NO: 48) produced half-maximal lysis of target cells at ~0.3 nM (FIG. 8C). A tumor cell line expressing MAGE-A1 and HLA-A28 was lysed by the CTL, but the lysis was lower than that obtained with cells infected with vaccinia-MAGE-A1 (FIG. 8C).

EXAMPLE 12

A Mage-A3 Peptide Presented by HLA-B40 to CTLS

Processing of Human Blood

Blood samples from donor LB 1841 (HLA-A3, -B35, -B40, Cw3, -Cw4) were processed as described in Example 6, except that:
1. the interphase containing the PBMC was harvested and then washed 3 times (or more) in cold phosphate buffer solution with 2 mM EDTA in order to eliminate the remaining platelets;
2. monocyte-derived dendritic cells (DC) were frozen on day 6. On the day of stimulation, DC were thawed and infected with a recombinant adenovirus encoding MAGE-A3, at a multiplicity of infection (MOI) of 500.

Isolation of CTL Clones Specific for MAGE-A3

Dendritic cells obtained from the blood sample of donor LB 1841 were infected with ALVAC-MAGE-A3 and coc-ultured with autologous CD8+ cells following essentially the same procedure as described in Example 7.

After several rounds of stimulation, the microculture was tested for specific lysis of autologous target cells following essentially the same procedure as described in Example 7, except that the vaccinia samples were sonicated for 30 seconds prior to use for infection of EBV-B target cells.

Microculture 526/F7, identified as containing cells that specifically lysed autologous EBV-B cells infected with vaccinia-MAGE-A3, was cloned by limiting dilution using, as stimulating cells, autologous EBV-B cells infected with recombinant ALVAC-MAGE-A3 (vCP1563) at a multiplic-ity of infection of 30 (the ALVAC-MAGE-A3 sample was also sonicated 30 sec before use), or with PHA, according to the following scheme:

First week: stimulators=ALVAC-MAGE-A3 (vCP1563) infected EBV-B cells in complete IMDM medium supplemented with 50 U IL-2/ml, 2.5 ng IL-12/ml and 5 U IL-4/ml;

Second week: stimulators=ALVAC-MAGE-A3 (vCP1563) infected EBV-B cells in complete IMDM medium supplemented with 50 U IL-2/ml;

Third week: PHA (0.5 µg/ml) in complete IMDM medium supplemented with 50 U/ml of IL-2;

Fourth week: PHA (0.5 µg/ml) in complete IMDM medium supplemented with 50 U/ml of IL-2, 5 ng/ml of IL-7+gentamicin (15 µg/ml)+MRA 0.5 g/ml (from ICN);

Fifth and sixth week: stimulators=EBV-B cells infected with Yersinia-MAGE-A3(aa147–314) and EBV-B cells infected with Yersinia-MAGE-A3(aa1–199) in complete IMDM medium supplemented with 50 U/ml of IL-2, 2.5 ng/ml of IL-12, 5 U/ml Il-4+gentamicin (15 µg/ml);

Seventh week and each week thereafter: PHA (0.2 µg/ml) in complete IMDM medium supplemented with 50 U/ml of IL-2, 5 U/ml of IL-4+gentamicin (15 µg/ml).

CTL clones were maintained in culture by weekly restimulation.

The clones were tested for specific lysis of autologous EBV-immortalized B cells infected with the vaccinia-MAGE-A3 construct, or with the parental vaccinia as a negative control. Clone LB1841 526/F7.1 was found positive (FIG. 9A) and was used in the following experiments.

The MAGE-A3 Epitope is Presented to CTL LB1841 526/F7.1 by HLA-B40

Figure 9A:
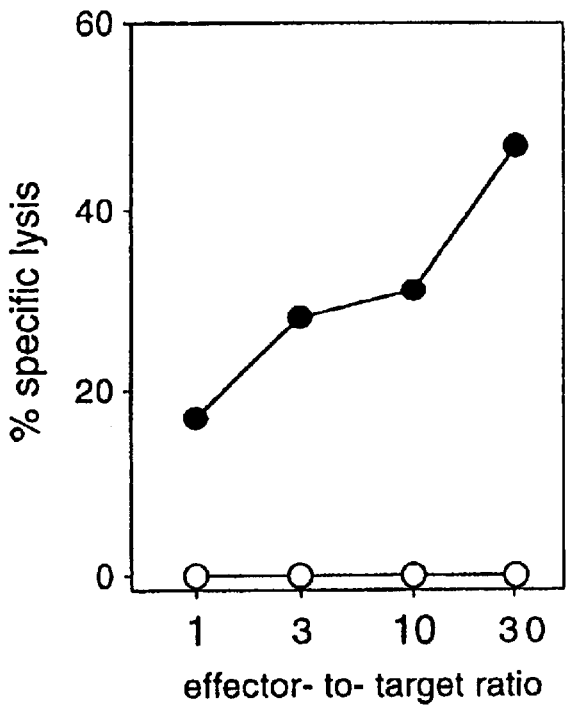
Figure 9B:
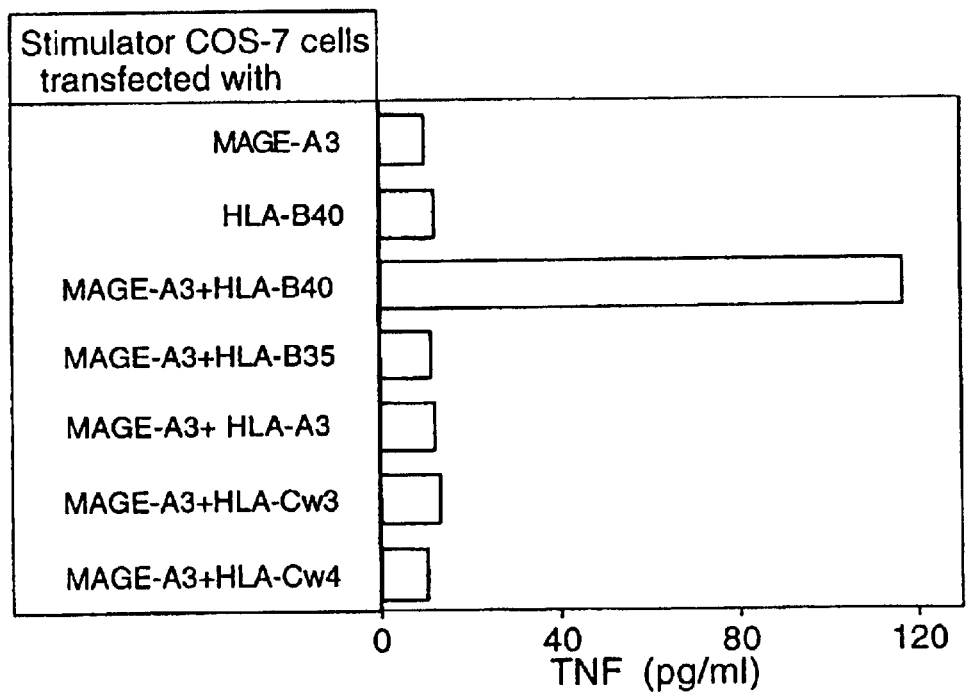

To identify the HLA molecule that presents the MAGE-A3 epitope recognized by CTL clone LB1841 526/F7.1, COS cells were transfected with the MAGE-A3 CDNA together with cDNAs coding for each of the putative HLA presenting molecules. In brief, 1.5×10⁴ cos cells distributed in microwells were cotransfected with 50 ng of plasmid pcDNA3-MAGE-A3, 50 ng of plasmid containing coding sequences for HLA molecules and 1 µl of Lipofectamine (Gibco BRL). The HLA coding sequences were isolated from various individuals; in particular, the HLA-B40 cDNA was obtained by RT-PCR using RNA from tumor cell line HA-7-RCC as a template. This PCR product cDNA was inserted in pCDNA3 (InVitrogen). The COS cells were incubated 24 hours at 37° C. and 8% CO$_2$. These transfectants were then tested for their ability to stimulate the production of TNF by clone LB1841 526/F7.1. Briefly, 2500 CTLs were added to the microwells containing the transfectants, in a total volume of 100 µl of Iscove's complete medium containing 25 U/ml of IL-2. After 24 hours, the supernatant was collected and the TNF content was determined by testing the cytotoxic effect of the supernatant on cells of WEHI-164 clone 13 in a standard MTT colorimetric assay. The cells transfected with both HLA-B40 and MAGE-A3 stimulated CTL clone LB1841 526/F7.1 to produce TNF (FIG. 9B). Cos cells transfected with MAGE-A3 or HLA-B40 alone did not stimulate the CTL clone.

Identification of the Antigenic Peptide

Figure 9C:
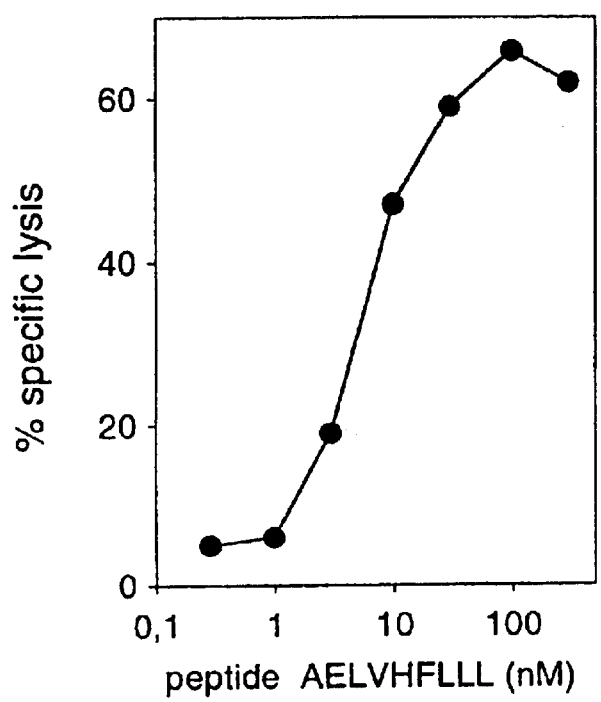

To identify the MAGE-A3 peptide recognized by CTL clone LB1841 526/F7.1, a set of peptides of 16 amino acids that overlapped by 12 amino acids and covered the entireMAGE-A3 protein sequence, was screened. Autologous EBV-B cells were incubated with each of these peptides at a concentration of 1 µg/ml, and tested for recognition by CTL clone LB1841 526/F7.1 in a chromium release assay at an effector to target cell ratio of 5:1. Peptide AALSRK-VAELVHFLLL (SEQ ID NO: 54) scored positive. The sequence of this peptide was screened for prediction of an HLA-B40 binding peptide with the software available at the website of the National Institute of Health. Peptide AELVH-FLLL (MAGE-A3 114–122) (SEQ ID NO: 55) had the highest score. It was tested in a cytotoxicity assay with CTL clone LB1841 526/F7.1 and produced half-maximal lysis of autologous EBV-B target cells at ~77 nM (FIG. 9C).

Recognition by CTL Clone LB1841 526/F7.1 of HLA-B40 Cells Expressing MAGE-A3

Figure 9D:
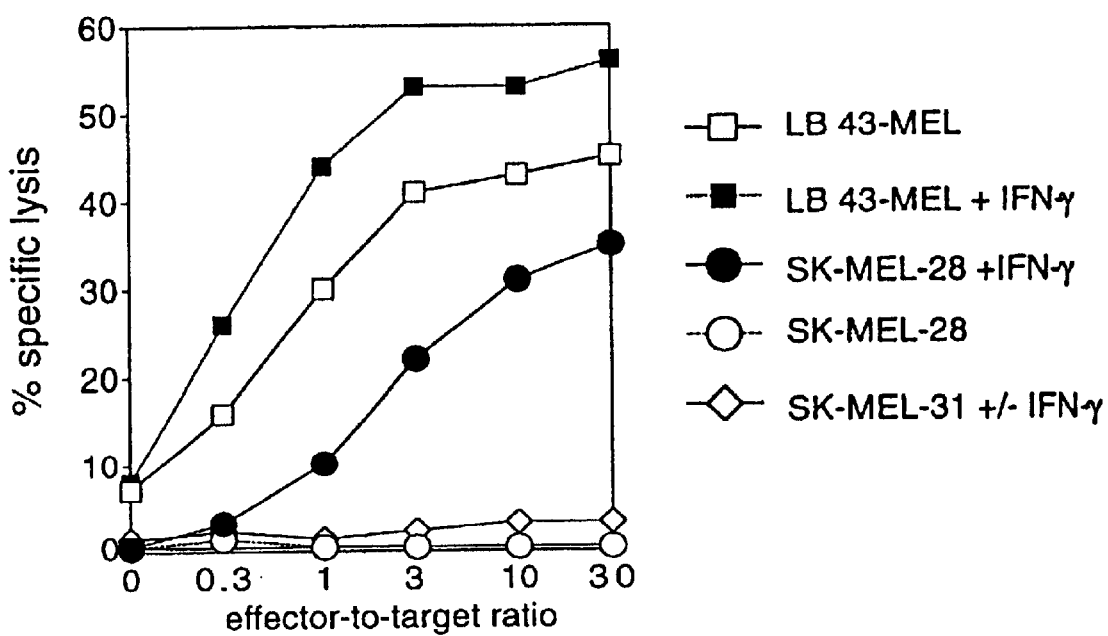

CTL clone LB1841 526/F7.1 was also able to lyse melanoma cell lines that expresses MAGE-A3 which were obtained from HLA-B40 positive patients, e.g., LB-43-MEL (FIG. 9D). Some melanoma cells, e.g., SK-MEL-28 and SK-31-MEL, were not lysed by clone LB1841 526/F7.1, even though the level of expression of MAGE-A3 appeared to be appropriate in these cells. The peptide-pulsed cells were also insensitive to the CTL lysis. The lack of lysis was likely due to downregulation of the HLA expression in these melanoma cells, since treatment of SK-MEL-28 cells with IFN-γ increased the lysis of these cells by clone LB1841 526/F7.1 (IFN-γ is known to upregulate HLA expression in certain cells).

EXAMPLE 13

A Mage-A1 Peptide Presented by HLA-B7 Molecules to Cytolytic T Lymphocytes

Processing of human blood

Blood samples from donor LB 1803 (HLA-A2, -A32, B7, -B60) were processed as described in Example 12.

Isolation of CTL Clones Specific for MAGE-A1

Dendritic cells obtained from the blood sample of donor LB 1803 were infected with ALVAC-MAGE-A1 and cocultured with autologous CD8+ cells following essentially the same procedure as described in Example 7 except that 15 µg/ml gentamycin was added to the culture medium.

After several rounds of stimulation, the microculture was tested for specific lysis of autologous target cells following essentially the same procedure as described in Example 7, except that the vaccinia samples were sonicated for 30 seconds prior to use for infection of EBV-B target cells.

Microculture 483/G8, identified as containing cells that specifically lysed autologous EBV-B cells infected with recombinant vaccinia (WR-MAGE-A1), was cloned by limiting dilution using, for the first two weekly stimulations, irradiated autologous EBV-B cells infected with Yersinia-MAGE-A1 as stimulating cells, irradiated LG2-EBV as feeder cells, IL-2 (50 U/ml) and gentamycin (15 µg/ml). CTL clones were then maintained in culture by weekly restimulation with PHA (0.5 µg/ml), feeder cells and IL-2.

The clones were tested for specific lysis of autologous EBV-immortalized B cells infected with recombinant vaccinia (WR-MAGE-A1), or with the parental vaccinia as a negative control. Clone LB1803 483/G8.4 was found positive (FIG. 10A) and was used in the following experiments.

The MAGE-A1 Epitope is Presented to CTL by HLA-H7 Molecules

Figure 10A:
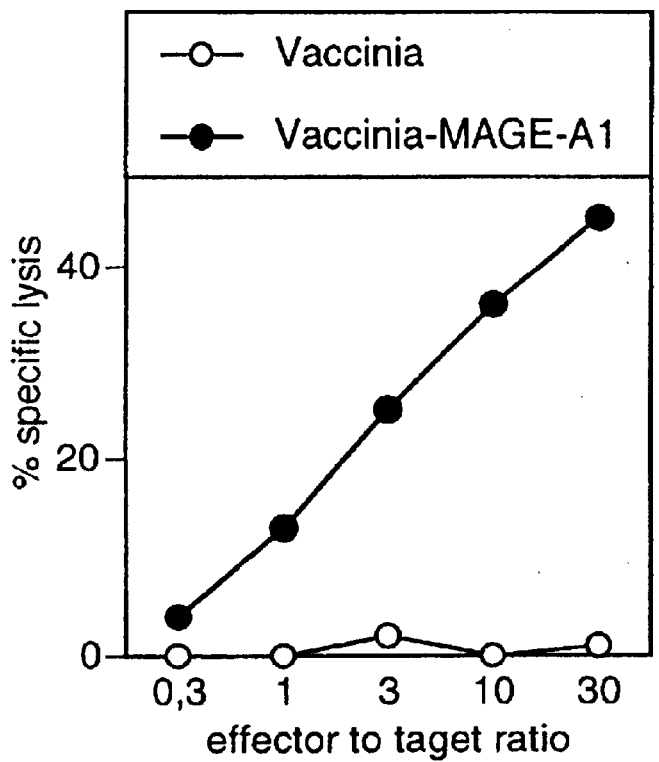
Figure 10B:
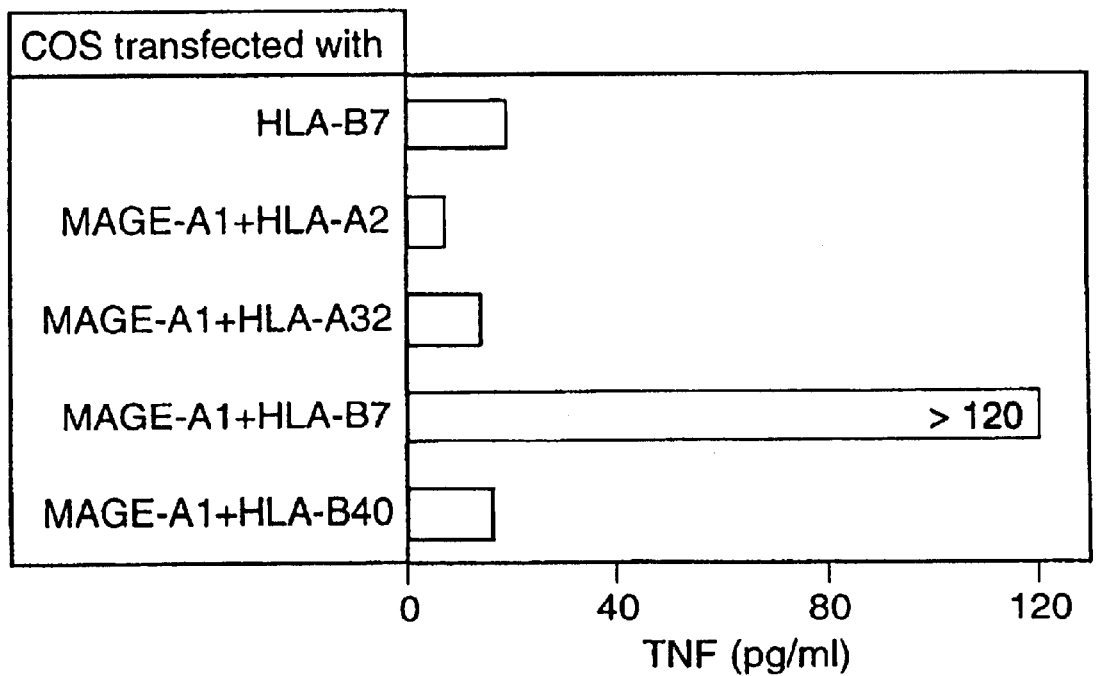

Donor LB 1803 was typed HLA-A2, -A32, -B7, -B60. To identify the HLA molecule that presents the MAGE-A1 epitope recognized by CTL clone LB1803 483/G8.4, COS-7 cells were transfected with the MAGE-A1 CDNA together with cDNAs coding for the putative HLA presenting molecules. In brief, 1.5×10$^4$ COS-7 cells distributed in microwells were cotransfected with 50 ng of plasmid pcDNA3-MAGE-A1, 50 ng of plasmid containing coding sequences for HLA molecules and 1 µl of Lipofectamine (Gibco BRL). The HLA coding sequences were isolated from various individuals; in particular, the HLA-B7 cDNA was obtained by RT-PCR using RNA from tumor cell line LB23-SAR as a template. This PCR product was inserted in pcDSRalpha. The transfected COS-7 cells were incubated 24 hours at 37° C. and 8% $CO^2$. These transfectants were then tested for their ability to stimulate the production of TNF by clone LB1803 483/G8.4. Briefly, 2000 CTL were added to the microwells containing the transfectant, in a total volume of 100 µl of Iscove's complete medium containing 25 U/ml of IL-2. After 24 hours, the supernatant was collected and the TNF content was determined by testing the cytotoxic effect of the supernatant on cells of WEHI-164 clone 13 in a standard MTT calorimetric assay. The cells transfected with both HLA-B7 and MAGE-A1 stimulated CTL clone LB1803 483/G8.4 to produce TNF (FIG. 10B). COS-7 cells transfected with HLA-B7 and either MAGE-A2, -A3, -A4, -A6, -A8, -A9, -A10, -A11, -A12, -B1, -B2, or -C2 were unable to stimulate CTL clone LB1803 483/G8.4 to produce TNF.

Identification of the Antigenic Peptide

To identify the MAGE-A1 peptide recognized by CTL clone LB1803 483/G8.4, a set of peptides of 12 amino acids, that overlapped by 8 amino acids and covered the entire MAGE-A1 protein sequence, was screened. Autologous EBV-B cells were incubated with each of these peptides at a concentration of 2 µg/ml, and tested for recognition by CTL clone LB 1803 483/G8.4 in a chromium release assay at an effector to target cell ratio of 20:1. Peptide RVRFFF-PSLREA (MAGE-A1 289–300) (SEQ ID NO: 56) scored positive. The sequence of this peptide was screened for an HLA-B7 binding peptide with the software available at the website of the National Institute of Health. Peptide RVR-FFFPSL (MAGE-A1 289–297) had the highest score. It was tested in a cytotoxicity assay with CTL clone LB1803 483/G8.4 (E/T ratio of 20:1) and produced half-maximal lysis of autologous EBV-B target cells at ~22 nM (FIG. 10D).

Recognition by CTL clone LB1803 483/G8.4 of HLA-B7 Cells Expressing MAGE-R1

CTL clone LB1803 483/G8.4 was also able to lyse HLA-B7 melanoma cell line ME275 clone 2 that expressed MAGE-A1 (FIG. 10D). Melanoma cell line ME190DA was also lysed but only after treatment for 72 h with 100 U/ml of IFN-gamma.

We claim:

1. An isolated nucleic acid molecule encoding the peptide GVYDREHTV, as set forth in SEQ ID NO: 44.

* * * * *

SEQUENCE LISTING

<160> NUMBER OF SEQ ID NOS: 57

<210> SEQ ID NO 1
<211> LENGTH: 9
<212> TYPE: PRT
<213> ORGANISM: Human MAGE-A1 peptide

<400> SEQUENCE: 1

Glu Ala Asp Pro Thr Gly His Ser Tyr
              5

<210> SEQ ID NO 2
<211> LENGTH: 9
<212> TYPE: PRT
<213> ORGANISM: Human MAGE-A1 peptide

<400> SEQUENCE: 2

```
Ser Ala Tyr Gly Glu Pro Arg Lys Leu
                 5
```

<210> SEQ ID NO 3
<211> LENGTH: 9
<212> TYPE: PRT
<213> ORGANISM: Human MAGE-A3 peptide

<400> SEQUENCE: 3

```
Glu Val Asp Pro Ile Gly His Leu Tyr
                 5
```

<210> SEQ ID NO 4
<211> LENGTH: 9
<212> TYPE: PRT
<213> ORGANISM: Human MAGE-A3 peptide

<400> SEQUENCE: 4

```
Phe Leu Trp Gly Pro Arg Ala Leu Val
                 5
```

<210> SEQ ID NO 5
<211> LENGTH: 10
<212> TYPE: PRT
<213> ORGANISM: Human MAGE-A3 peptide

<400> SEQUENCE: 5

```
Met Glu Val Asp Pro Ile Gly His Leu Tyr
                 5                  10
```

<210> SEQ ID NO 6
<211> LENGTH: 9
<212> TYPE: PRT
<213> ORGANISM: Human BAGE peptide

<400> SEQUENCE: 6

```
Ala Ala Arg Ala Val Phe Leu Ala Leu
                 5
```

<210> SEQ ID NO 7
<211> LENGTH: 8
<212> TYPE: PRT
<213> ORGANISM: Human GAGE-1,2 peptide

<400> SEQUENCE: 7

```
Tyr Arg Pro Arg Pro Arg Arg Tyr
                 5
```

<210> SEQ ID NO 8
<211> LENGTH: 10
<212> TYPE: PRT
<213> ORGANISM: Human RAGE peptide

<400> SEQUENCE: 8

```
Ser Pro Ser Ser Asn Arg Ile Arg Asn Thr
                 5                  10
```

<210> SEQ ID NO 9
<211> LENGTH: 10
<212> TYPE: PRT
<213> ORGANISM: Human GnT-V peptide

<400> SEQUENCE: 9

```
Val Leu Pro Asp Val Phe Ile Arg Cys Val
                 5                  10
```

<210> SEQ ID NO 10
<211> LENGTH: 9
<212> TYPE: PRT
<213> ORGANISM: Human MUM-1 peptide

<400> SEQUENCE: 10

Glu Glu Lys Leu Ile Val Val Leu Phe
                5

<210> SEQ ID NO 11
<211> LENGTH: 9
<212> TYPE: PRT
<213> ORGANISM: Human MUM-1 peptide

<400> SEQUENCE: 11

Glu Glu Lys Leu Ser Val Val Leu Phe
                5

<210> SEQ ID NO 12
<211> LENGTH: 10
<212> TYPE: PRT
<213> ORGANISM: Human CDK4 peptide

<400> SEQUENCE: 12

Ala Cys Asp Pro His Ser Gly His Phe Val
                5                   10

<210> SEQ ID NO 13
<211> LENGTH: 10
<212> TYPE: PRT
<213> ORGANISM: Human CDK4 peptide

<400> SEQUENCE: 13

Ala Arg Asp Pro His Ser Gly His Phe Val
                5                   10

<210> SEQ ID NO 14
<211> LENGTH: 9
<212> TYPE: PRT
<213> ORGANISM: Human  -catenin peptide

<400> SEQUENCE: 14

Ser Tyr Leu Asp Ser Gly Ile His Phe
                5

<210> SEQ ID NO 15
<211> LENGTH: 9
<212> TYPE: PRT
<213> ORGANISM: Human  -catenin peptide

<400> SEQUENCE: 15

Ser Tyr Leu Asp Ser Gly Ile His Ser
                5

<210> SEQ ID NO 16
<211> LENGTH: 9
<212> TYPE: PRT
<213> ORGANISM: Human Tyrosinase peptide

<400> SEQUENCE: 16

Met Leu Leu Ala Val Leu Tyr Cys Leu
                5

```
<210> SEQ ID NO 17
<211> LENGTH: 9
<212> TYPE: PRT
<213> ORGANISM: Human Tyrosinase peptide

<400> SEQUENCE: 17

Tyr Met Asn Gly Thr Met Ser Gln Val
                5

<210> SEQ ID NO 18
<211> LENGTH: 9
<212> TYPE: PRT
<213> ORGANISM: Human Tyrosinase peptide

<400> SEQUENCE: 18

Tyr Met Asp Gly Thr Met Ser Gln Val
                5

<210> SEQ ID NO 19
<211> LENGTH: 9
<212> TYPE: PRT
<213> ORGANISM: Human Tyrosinase peptide

<400> SEQUENCE: 19

Ala Phe Leu Pro Trp His Arg Leu Phe
                5

<210> SEQ ID NO 20
<211> LENGTH: 9
<212> TYPE: PRT
<213> ORGANISM: Human Tyrosinase peptide

<400> SEQUENCE: 20

Ser Glu Ile Trp Arg Asp Ile Asp Phe
                5

<210> SEQ ID NO 21
<211> LENGTH: 9
<212> TYPE: PRT
<213> ORGANISM: Human Tyrosinase peptide

<400> SEQUENCE: 21

Tyr Glu Ile Trp Arg Asp Ile Asp Phe
                5

<210> SEQ ID NO 22
<211> LENGTH: 15
<212> TYPE: PRT
<213> ORGANISM: Human Tyrosinase peptide

<400> SEQUENCE: 22

Gln Asn Ile Leu Leu Ser Asn Ala Pro Leu Gly Pro Gln Phe Pro
                5                   10                  15

<210> SEQ ID NO 23
<211> LENGTH: 15
<212> TYPE: PRT
<213> ORGANISM: Human Tyrosinase peptide

<400> SEQUENCE: 23

Asp Tyr Ser Tyr Leu Gln Asp Ser Asp Pro Asp Ser Phe Gln Asp
                5                   10                  15

<210> SEQ ID NO 24
<211> LENGTH: 10
```

```
<212> TYPE: PRT
<213> ORGANISM: Human Melan-AMART-1 peptide

<400> SEQUENCE: 24

Glu Ala Ala Gly Ile Gly Ile Leu Thr Val
                5                   10

<210> SEQ ID NO 25
<211> LENGTH: 9
<212> TYPE: PRT
<213> ORGANISM: Human Melan-AMART-1 peptide

<400> SEQUENCE: 25

Ile Leu Thr Val Ile Leu Gly Val Leu
                5

<210> SEQ ID NO 26
<211> LENGTH: 9
<212> TYPE: PRT
<213> ORGANISM: Human gp100Pmel117 peptide

<400> SEQUENCE: 26

Lys Thr Trp Gly Gln Tyr Trp Gln Val
                5

<210> SEQ ID NO 27
<211> LENGTH: 9
<212> TYPE: PRT
<213> ORGANISM: Human gp100Pmel117 peptide

<400> SEQUENCE: 27

Ile Thr Asp Gln Val Pro Phe Ser Val
                5

<210> SEQ ID NO 28
<211> LENGTH: 9
<212> TYPE: PRT
<213> ORGANISM: Human gp100Pmel117 peptide

<400> SEQUENCE: 28

Tyr Leu Glu Pro Gly Pro Val Thr Ala
                5

<210> SEQ ID NO 29
<211> LENGTH: 10
<212> TYPE: PRT
<213> ORGANISM: Human gp100Pmel117 peptide

<400> SEQUENCE: 29

Leu Leu Asp Gly Thr Ala Thr Leu Arg Leu
                5                   10

<210> SEQ ID NO 30
<211> LENGTH: 10
<212> TYPE: PRT
<213> ORGANISM: Human gp100Pmel117 peptide

<400> SEQUENCE: 30

Val Leu Tyr Arg Tyr Gly Ser Phe Ser Val
                5                   10

<210> SEQ ID NO 31
<211> LENGTH: 9
<212> TYPE: PRT
<213> ORGANISM: Human DAGE peptide
```

<400> SEQUENCE: 31

Leu Tyr Val Asp Ser Leu Phe Phe Leu
                  5

<210> SEQ ID NO 32
<211> LENGTH: 12
<212> TYPE: PRT
<213> ORGANISM: Human MAGE-A6 peptide

<400> SEQUENCE: 32

Lys Ile Ser Gly Gly Pro Arg Ile Ser Tyr Pro Leu
                  5                  10

<210> SEQ ID NO 33
<211> LENGTH: 31
<212> TYPE: DNA
<213> ORGANISM: Human MAGE-A1 primer

<400> SEQUENCE: 33
aaactgcaga tgtctcttga gcagaggagt c                                31

<210> SEQ ID NO 34
<211> LENGTH: 30
<212> TYPE: DNA
<213> ORGANISM: Human MAGE-A1 primer

<400> SEQUENCE: 34
aaactgcagt cagactccct cttcctcctc                                  30

<210> SEQ ID NO 35
<211> LENGTH: 32
<212> TYPE: DNA
<213> ORGANISM: Human MAGE-A4 primer

<400> SEQUENCE: 35
aaaaactgca gatgtcttct gagcagaaga gt                               32

<210> SEQ ID NO 36
<211> LENGTH: 29
<212> TYPE: DNA
<213> ORGANISM: Human MAGE-A4 primer

<400> SEQUENCE: 36
aaaaaatcga ttcagactcc ctcttcctc                                   29

<210> SEQ ID NO 37
<211> LENGTH: 16
<212> TYPE: PRT
<213> ORGANISM: Human MAGE-A1 peptide

<400> SEQUENCE: 37

Asp Gly Arg Glu His Ser Ala Tyr Gly Glu Pro Arg Lys Leu Leu Thr
 1               5                  10                  15

<210> SEQ ID NO 38
<211> LENGTH: 16
<212> TYPE: PRT
<213> ORGANISM: Human MAGE-A1 peptide

<400> SEQUENCE: 38

Gln Val Pro Asp Ser Asp Pro Ala Arg Tyr Glu Phe Leu Trp Gly Pro
 1               5                  10                  15

<210> SEQ ID NO 39
<211> LENGTH: 16
<212> TYPE: PRT
<213> ORGANISM: Human MAGE-A1 peptide

<400> SEQUENCE: 39

Ser Asp Pro Ala Arg Tyr Glu Phe Leu Trp Gly Pro Arg Ala Leu Ala
 1               5                  10                  15

<210> SEQ ID NO 40
<211> LENGTH: 16
<212> TYPE: PRT
<213> ORGANISM: Human MAGE-A4 peptide

<400> SEQUENCE: 40

Gly Ser Asn Pro Ala Arg Tyr Glu Phe Leu Trp Gly Pro Arg Ala Leu
 1               5                  10                  15

<210> SEQ ID NO 41
<211> LENGTH: 10
<212> TYPE: PRT
<213> ORGANISM: Human MAGE-A1 peptide

<400> SEQUENCE: 41

Ser Asp Pro Ala Arg Tyr Glu Phe Leu Trp
 1               5                  10

<210> SEQ ID NO 42
<211> LENGTH: 9
<212> TYPE: PRT
<213> ORGANISM: Human MAGE-A1 peptide

<400> SEQUENCE: 42

Asp Pro Ala Arg Tyr Glu Phe Leu Trp
 1               5

<210> SEQ ID NO 43
<211> LENGTH: 130
<212> TYPE: DNA
<213> ORGANISM: Human MAGE-A4 primer

<400> SEQUENCE: 43

```
tgatgggagg gagcacactg tctatgggga gcccaggaaa ctgctcaccc aagattgggt      60
gcaggaaaac tacctggagt accggcaggt acccggcagt aatcctgcgc gctatgagtt     120
cctgtggggt                                                            130
```

<210> SEQ ID NO 44
<211> LENGTH: 10
<212> TYPE: PRT
<213> ORGANISM: Human MAGE-A4 peptide

<400> SEQUENCE: 44

Gly Val Tyr Asp Gly Arg Glu His Thr Val
 1               5                  10

<210> SEQ ID NO 45
<211> LENGTH: 12
<212> TYPE: PRT
<213> ORGANISM: Human MAGE-A1 peptide

<400> SEQUENCE: 45

Ala Ser Ala Phe Pro Thr Thr Ile Asn Phe Thr Arg
 1               5                  10

<210> SEQ ID NO 46
<211> LENGTH: 16
<212> TYPE: PRT
<213> ORGANISM: Human MAGE-A1 peptide

<400> SEQUENCE: 46

Ser Pro Gln Gly Ala Ser Ala Phe Pro Thr Thr Ile Asn Phe Thr Arg
 1               5                  10                  15

<210> SEQ ID NO 47
<211> LENGTH: 9
<212> TYPE: PRT
<213> ORGANISM: Human MAGE-A1 peptide

<400> SEQUENCE: 47

Ser Ala Phe Pro Thr Thr Ile Asn Phe
 1               5

<210> SEQ ID NO 48
<211> LENGTH: 10
<212> TYPE: PRT
<213> ORGANISM: Human MAGE-A1 peptide

<400> SEQUENCE: 48

Glu Val Tyr Asp Gly Arg Glu His Ser Ala
 1               5                  10

<210> SEQ ID NO 49
<211> LENGTH: 961
<212> TYPE: DNA
<213> ORGANISM: Human MAGE-A4 partial

<400> SEQUENCE: 49
agtcatcatg tcttctgagc agaagagtca gcactgcaag cctgaggaag gcgttgaggc      60
ccaagaagag gccctgggcc tggtgggtgc acaggctcct actactgagg agcaggaggc     120
tgctgtctcc tcctcctctc tctggtccc tggcaccctg gaggaagtgc ctgctgctga     180
gtcagcaggt cctccccaga gtcctcaggg agcctctgcc ttacccacta ccatcagctt     240
cacttgctgg aggcaaccca atgagggttc agcagccaa gagaggagg ggccaagcac     300
ctcgcctgac gcagagtcct tgttccgaga agcactcagt aacaaggtgg atgagttggc     360
tcatttttctg ctccgcaagt atcgagccaa ggagctggtc acaaaggcag aaatgctgga     420
gagagtcatc aaaaattaca agcgctgctt tcctgtgatc ttcggcaaag cctccgagtc     480
cctgaagatg atctttggca ttgacgtgaa ggaagtggac cccgccagca acacctacac     540
ccttgtcacc tgcctgggcc tttcctatga tggcctgctg ggtaataatc agatctttcc     600
caagacaggc cttctgataa tcgtcctggg cacaattgca atgggaggcg acagcgcctc     660
tgaggaggaa atctgggagg agctgggtgt gatgggggtg tatgatggga gggagcacac     720
tgtctatggg gagcccagga aactgctcac ccaagattgg gtgcaggaaa actacctgga     780
gtaccggcag gtacccggca gtaatcctgc gcgctatgag ttcctgtggg gtccaagggc     840
tctggctgaa accagctatg tgaaagtcct ggagcatgtg gtcagggtca atgcaagagt     900
tcgcattgcc tacccatccc tgcgtgaagc agctttgtta gaggaggaag agggagtctg     960
a                                                                       961

<210> SEQ ID NO 50
<211> LENGTH: 31

```
<212> TYPE: DNA
<213> ORGANISM: Human MAGE-A3 primer

<400> SEQUENCE: 50
aactgcagtt tcctgtgatc ttcagcaaag c                              31

<210> SEQ ID NO 51
<211> LENGTH: 29
<212> TYPE: DNA
<213> ORGANISM: Human MAGE-A3 primer

<400> SEQUENCE: 51
ccatcgattc actcttcccc ctctctcaa                                 29

<210> SEQ ID NO 52
<211> LENGTH: 30
<212> TYPE: DNA
<213> ORGANISM: Human MAGE-A3 primer

<400> SEQUENCE: 52
accagagtca tcctgcagat gcctcttgag                                30

<210> SEQ ID NO 53
<211> LENGTH: 33
<212> TYPE: DNA
<213> ORGANISM: Human MAGE-A3 primer

<400> SEQUENCE: 53
gcctgccttg ggatcgattc acatgatctg att                            33

<210> SEQ ID NO 54
<211> LENGTH: 16
<212> TYPE: PRT
<213> ORGANISM: Human MAGE-A3 peptide

<400> SEQUENCE: 54

Ala Ala Leu Ser Arg Lys Val Ala Glu Leu Val His Phe Leu Leu Leu
 1               5                  10                  15

<210> SEQ ID NO 55
<211> LENGTH: 9
<212> TYPE: PRT
<213> ORGANISM: Human MAGE-A3 peptide

<400> SEQUENCE: 55

Ala Glu Leu Val His Phe Leu Leu Leu
 1               5

<210> SEQ ID NO 56
<211> LENGTH: 12
<212> TYPE: PRT
<213> ORGANISM: Human MAGE-A1 peptide

<400> SEQUENCE: 56

Arg Val Arg Phe Phe Phe Pro Ser Leu Arg Glu Ala
 1               5                  10

<210> SEQ ID NO 57
<211> LENGTH: 9
<212> TYPE: PRT
<213> ORGANISM: Human MAGE-A1 peptide
```

-continued

```
<400> SEQUENCE: 57

Arg Val Arg Phe Phe Phe Pro Ser Leu
 1               5
```